(12) United States Patent
Fan

(10) Patent No.: US 9,114,004 B2
(45) Date of Patent: *Aug. 25, 2015

(54) FLEXIBLE ARTIFICIAL RETINA DEVICES

(75) Inventor: Long-Sheng Fan, Hsinchu (TW)

(73) Assignee: IRIDIUM MEDICAL TECHNOLOGY CO, LTD., Hsinchu (TW)

( * ) Notice: Subject to any disclaimer, the term of this patent is extended or adjusted under 35 U.S.C. 154(b) by 147 days.

This patent is subject to a terminal disclaimer.

(21) Appl. No.: 13/282,423

(22) Filed: Oct. 26, 2011

(65) Prior Publication Data

US 2012/0109296 A1   May 3, 2012

Related U.S. Application Data

(63) Continuation-in-part of application No. 13/102,596, filed on May 6, 2011, now abandoned.

(60) Provisional application No. 61/407,229, filed on Oct. 27, 2010.

(51) Int. Cl.
*A61F 2/14* (2006.01)
*A61F 9/08* (2006.01)
*A61F 9/007* (2006.01)
(Continued)

(52) U.S. Cl.
CPC ............ *A61F 2/14* (2013.01); *A61F 9/00727* (2013.01); *A61F 9/08* (2013.01); *A61N 1/0543* (2013.01); *A61F 9/0017* (2013.01)

(58) Field of Classification Search
CPC ......... A61F 9/08; A61F 9/00727; A61F 2/14; A61F 9/0017; A61F 2210/0076; A61F 2250/0001; A61F 2250/0002; A61F 2250/0026; A61F 2250/0091; A61N 1/36046; A61N 1/0543
USPC ...................................... 623/6.63; 607/53, 54
See application file for complete search history.

(56) References Cited

U.S. PATENT DOCUMENTS

| 5,476,494 A | * | 12/1995 | Edell et al. ............... 607/116 |
| 5,650,363 A | | 7/1997 | Endroes et al. |
| 5,840,199 A | | 11/1998 | Warren |

(Continued)

FOREIGN PATENT DOCUMENTS

JP     2006-051164     2/2006

OTHER PUBLICATIONS

Zrenner, Eberhart et al., "Subretinal electronic chips allow blind patients to read letters and combine them to words," Proceedings of the Royal Society B, 2011, 278, 1489-1497, downloaded from http://rspb.royalsocietypublishing.org/, Jul. 18, 2011.

(Continued)

*Primary Examiner* — Paul Prebilic
(74) *Attorney, Agent, or Firm* — Blakely Sokoloff Taylor Zafman LLP

(57) ABSTRACT

An implant apparatus comprising a plurality of photo sensors, a plurality of micro electrodes and circuitry coupled to the photo sensors and the micro electrodes are described. The photo sensors may receive incoming light. The circuit may drive the micro electrodes to stimulate neuron cells for enabling perception of a vision of the light captured by the photo sensors. The apparatus may be implemented in a flexible material to conform to a shape of a human eyeball to allow the micro electrodes aligned with the neuron cells for the stimulation.

23 Claims, 21 Drawing Sheets

(51) Int. Cl.
*A61N 1/05* (2006.01)
*A61F 9/00* (2006.01)

(56) References Cited

U.S. PATENT DOCUMENTS

| | | | |
|---|---|---|---|
| 6,068,632 | A | 5/2000 | Carchidi et al. |
| 6,150,676 | A * | 11/2000 | Sasaki ............... 257/191 |
| 6,294,831 | B1 | 9/2001 | Shishido et al. |
| 6,324,429 | B1 | 11/2001 | Shire et al. |
| 7,035,692 | B1 | 4/2006 | Maghribi et al. |
| 7,079,900 | B2 | 7/2006 | Greenburg et al. |
| 7,113,661 | B2 | 9/2006 | Arai et al. |
| 7,127,301 | B1 | 10/2006 | Okandan et al. |
| 7,130,693 | B1 | 10/2006 | Montalbo |
| 7,158,836 | B2 | 1/2007 | Suzuki |
| 7,840,274 | B2 | 11/2010 | Greenberg et al. |
| 7,914,842 | B1 | 3/2011 | Greenberg et al. |
| 8,142,190 | B2 | 3/2012 | Anitua Aldecoa |
| 8,150,526 | B2 * | 4/2012 | Gross et al. ............... 607/54 |
| 8,209,023 | B2 * | 6/2012 | Zhou et al. ............... 607/53 |
| 8,322,027 | B1 | 12/2012 | Greenberg et al. |
| 2002/0091422 | A1 | 7/2002 | Greenberg et al. |
| 2002/0094508 | A1 | 7/2002 | Lorenzi |
| 2002/0099420 | A1 | 7/2002 | Chow et al. |
| 2002/0111655 | A1 | 8/2002 | Scribner |
| 2003/0114904 | A1 | 6/2003 | Ovadia et al. |
| 2003/0160303 | A1 | 8/2003 | Hirokawa et al. |
| 2003/0209792 | A1 | 11/2003 | Takaishi |
| 2005/0082684 | A1 | 4/2005 | Aiba et al. |
| 2005/0161818 | A1 | 7/2005 | Basceri |
| 2006/0184245 | A1 * | 8/2006 | Graf et al. ............... 623/6.63 |
| 2006/0241753 | A1 | 10/2006 | Suaning et al. |
| 2006/0273304 | A1 | 12/2006 | Cok |
| 2007/0142877 | A1 | 6/2007 | McLean |
| 2007/0257373 | A1 | 11/2007 | Akram et al. |
| 2008/0058897 | A1 | 3/2008 | McMahon et al. |
| 2008/0065208 | A1 | 3/2008 | Greenberg et al. |
| 2008/0086206 | A1 | 4/2008 | Nasiatka et al. |
| 2008/0288067 | A1 | 11/2008 | Flood |
| 2008/0294224 | A1 | 11/2008 | Greenberg et al. |
| 2009/0264972 | A1 * | 10/2009 | Zhou et al. ............... 607/116 |
| 2009/0326594 | A1 | 12/2009 | North et al. |
| 2010/0184285 | A1 | 7/2010 | Hua et al. |
| 2010/0204754 | A1 | 8/2010 | Gross et al. |
| 2010/0298895 | A1 * | 11/2010 | Ghaffari et al. ............... 607/3 |
| 2011/0172736 | A1 * | 7/2011 | Gefen et al. ............... 607/54 |
| 2011/0307042 | A1 * | 12/2011 | DeCarmine ............... 607/116 |

OTHER PUBLICATIONS

Shire, Douglas B. et al., "Development and Implantation of a Minimally Invasive Wireless Subretinal Neurostimulator," IEEE Transactions on Biomedical Engineering, vol. 56, No. 10, Oct. 2009.

Ahuja, A. K., et al., "Blind subjects implanted with the Argus II retinal prosthesis are able to improve performance in a spatial-motor task," British Journal of Ophthalmology, 95:539-543, Sep. 29, 2010, downloaded from http://bjo.bmj.com/, Jul. 28, 2011.

Fan, L.-S. et al., "Monolithically Integrated Flexible Artificial Retina Microsystems Technology and in vitro Characterization," Association for Research in Vision and Ophthalmology, ARVO 2010, May 2-6, 2010, Ft. Lauderdale, Florida, USA, abstract.

Fan, Long-Sheng et al., "A Flexible & Translucent CMOS Retinal Prosthesis and in vitro Characterization," Association for Research in Vision and Ophthalmology, ARVO 2011, May 1-5, 2011, Ft. Lauderdale, Florida, USA, abstract.

Fan, L.-S. et al., "A Flexible Sensing CMOS Technology for Sensor-Integrated, Intelligent Retinal Prosthesis," Asia-Pacific Conference on Vision, APCV 2010, Jul. 23-26, 2010, Taipei, Taiwan, abstract.

International Search Report and Written Opinion mailed Apr. 25, 2012, for International Application No. PCT/US2011/058159, 20 pages.

Ng, David C. et al., "Impantable Microimagers," Sensors 2008, 8(5), 3183-3204, May 15, 2008.

Tokuda, Takashi et al., "Flexible and extendible neural interface device based on cooperative multi-chip CMOS LSI architecture," Sensors and Actuators A 122 (2005), 88-98, May 25, 2005.

International Search Report and Written Opinion mailed Jul. 6, 2012, for International Patent Application No. PCT/US2011/064014, 18 pages.

The Association for Research in Vision and Ophtalmology, Late Breaking Abstracts, for Sight: The Future of Eye and Vision Research, May 2-6, 2010.

Chichilnisky, et al., "Functional Asymmetries in ON and OFF Ganglion Cells of Primate Retina", *The Journal of Neuroscience*, 22(7), (Apr. 1, 2002), pp. 2737-2747.

Graf, "Bendable Electronics for Retinal Implants", *Ultra-thin Chip Technology and Applications*, Chapter 28, Springer New York, (Nov. 12, 2010), pp. 363-375.

* cited by examiner

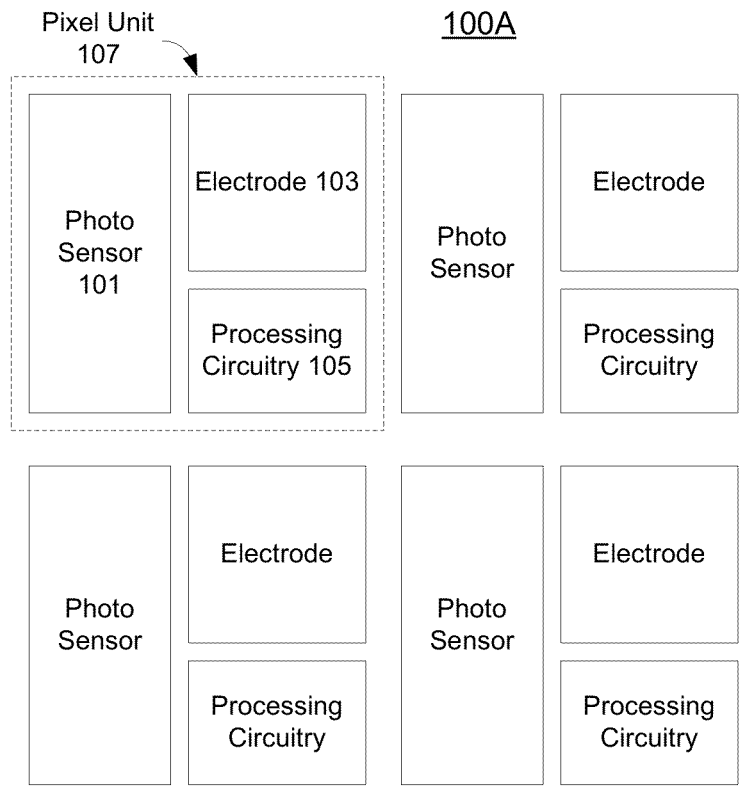
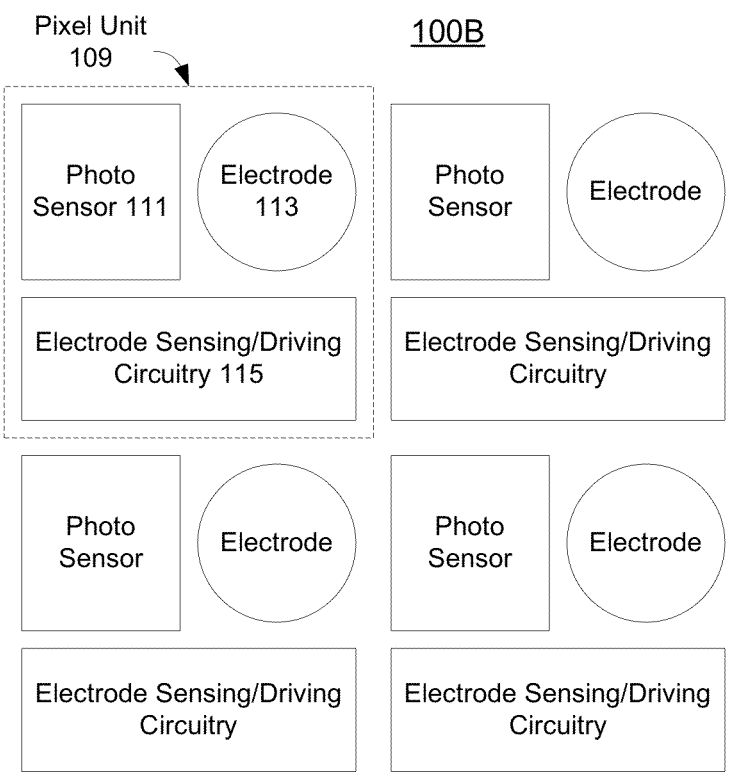
Fig. 1A
Fig. 1B

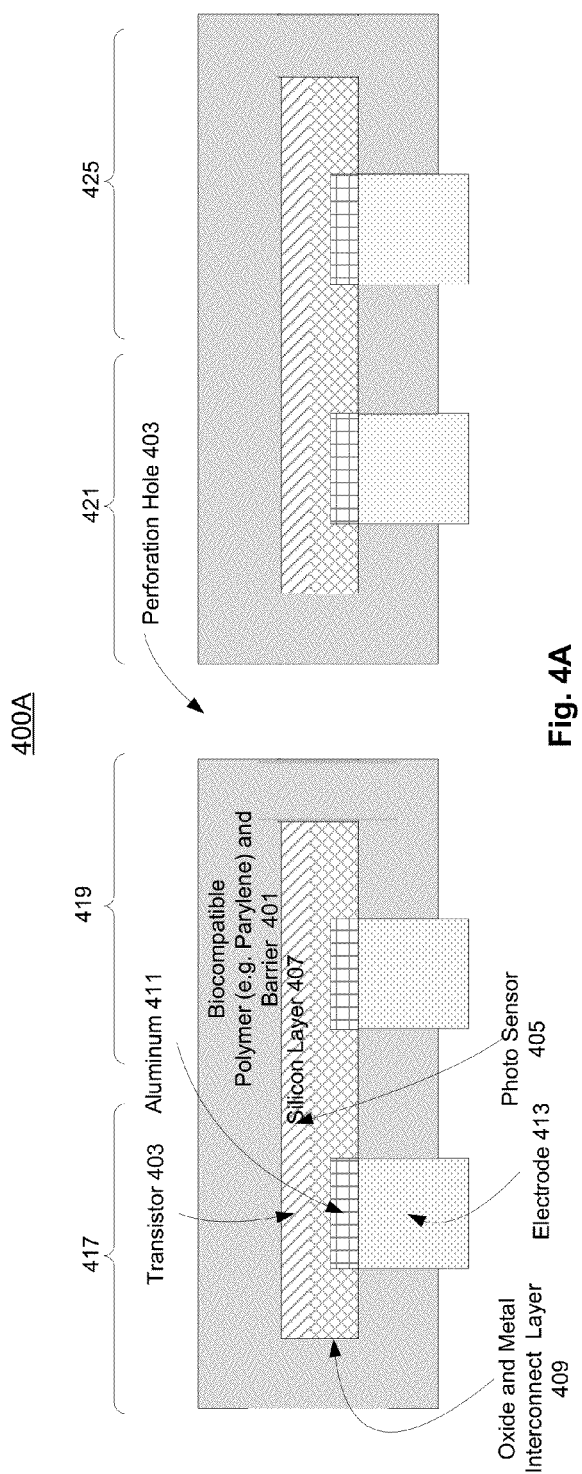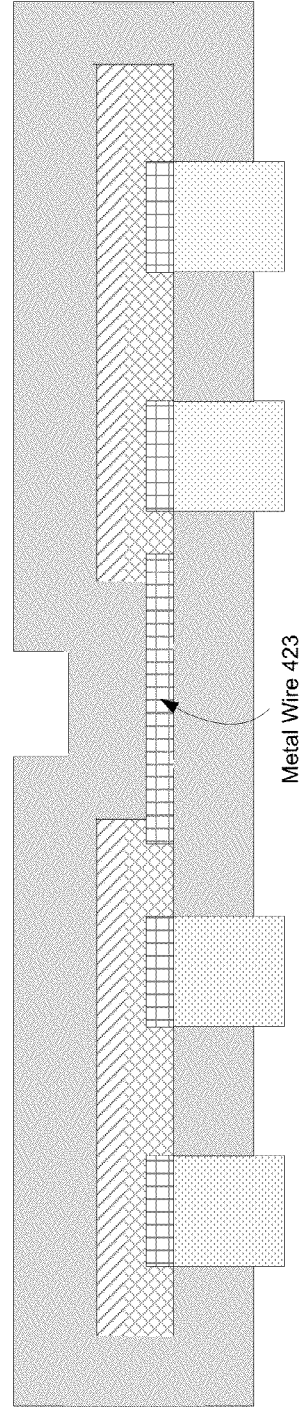

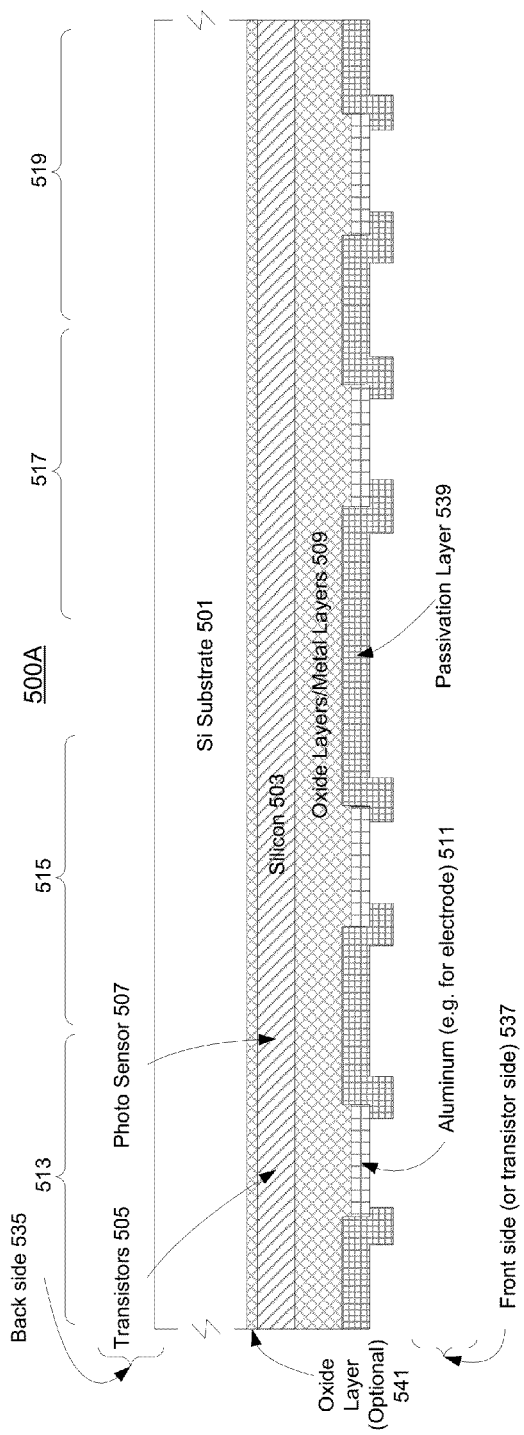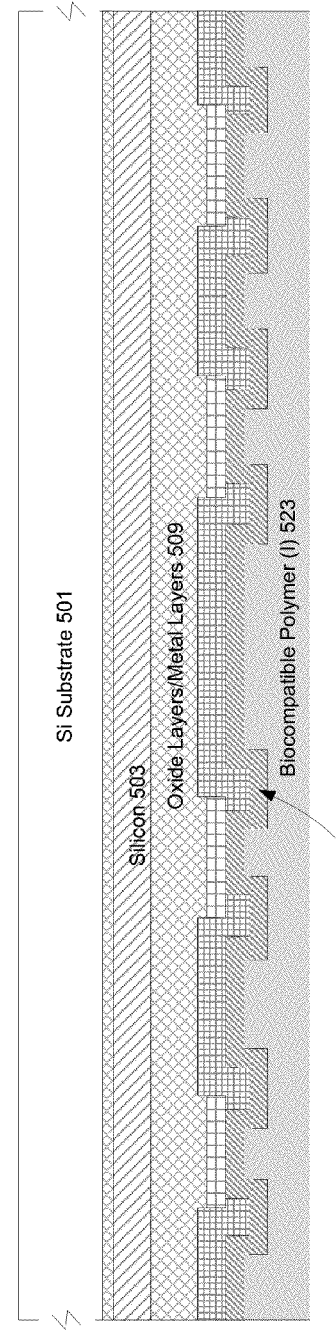

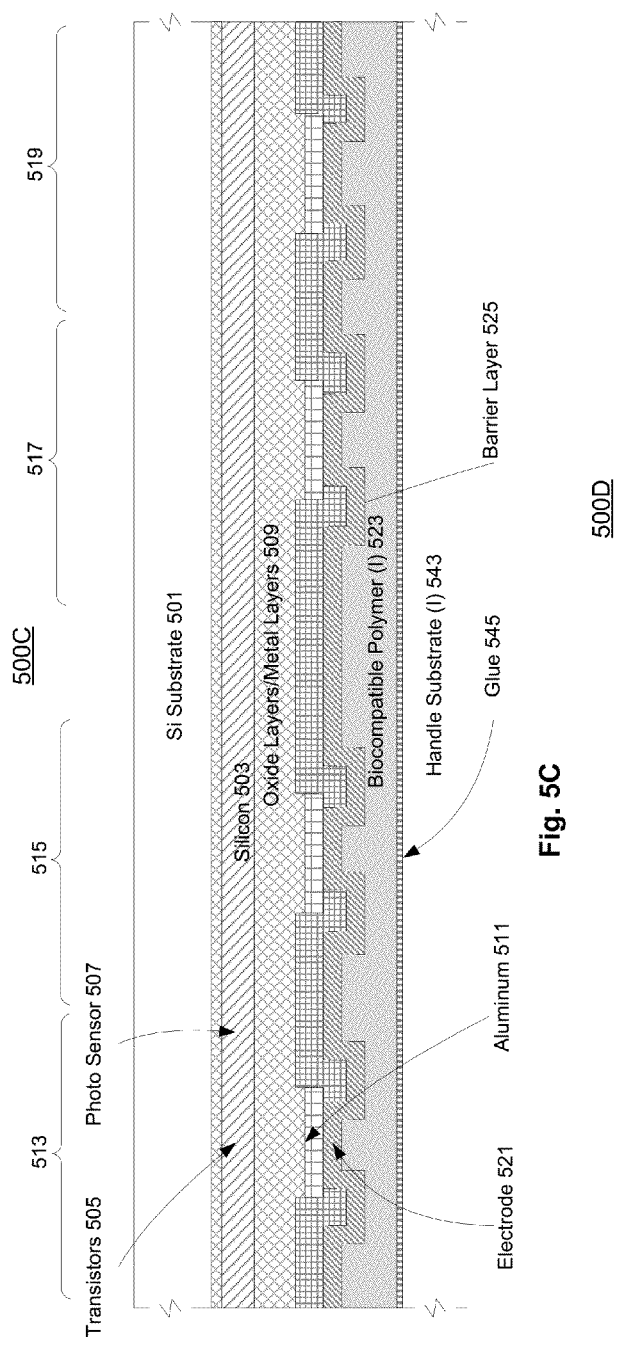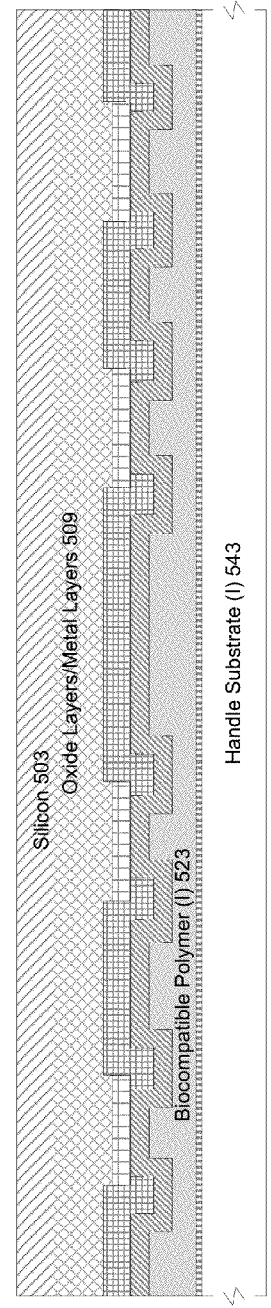

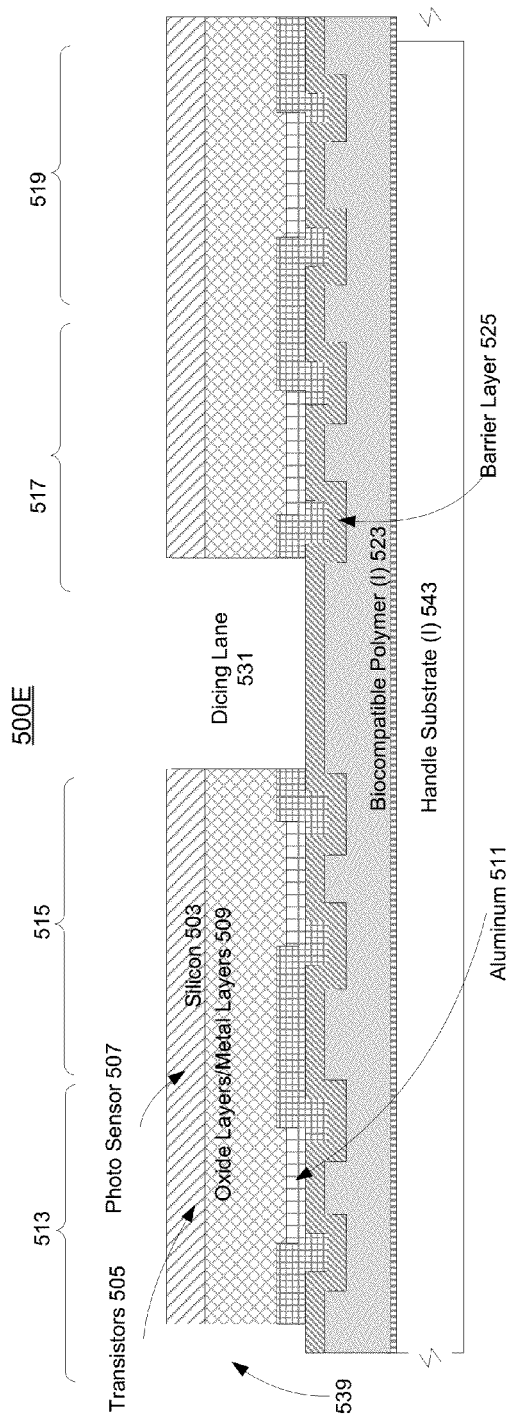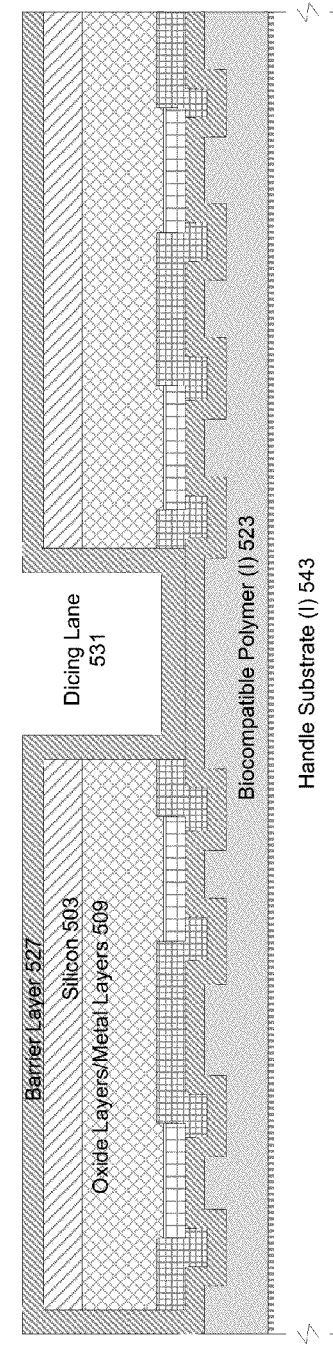

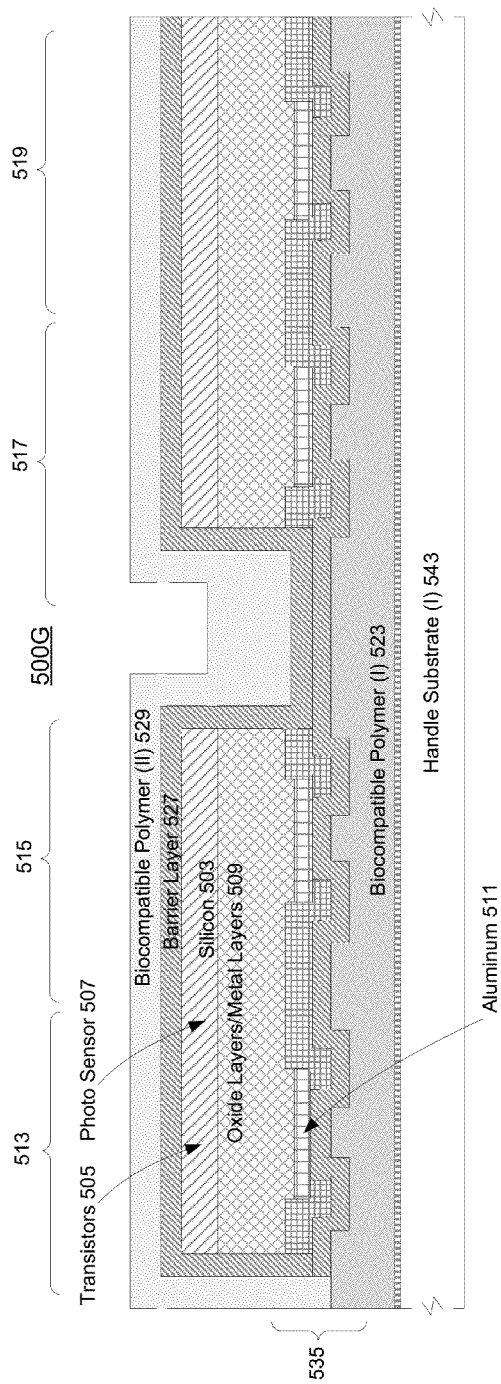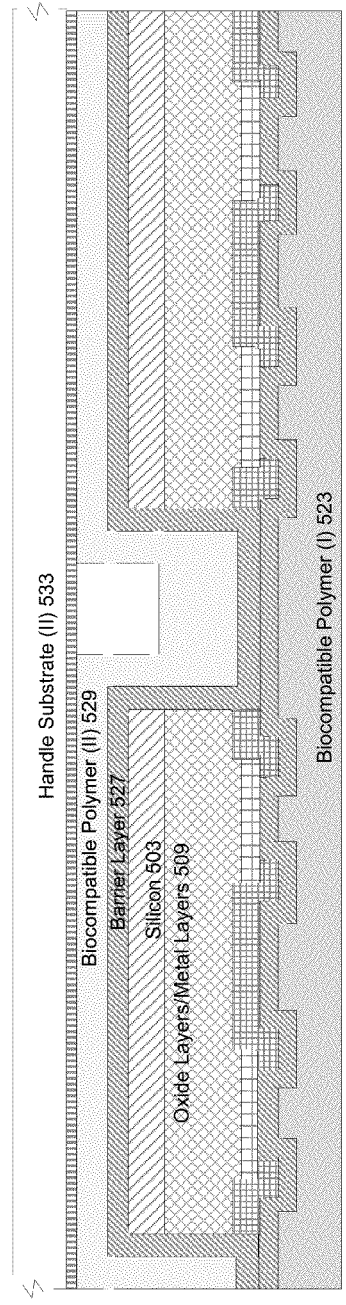
Fig. 5G
Fig. 5H

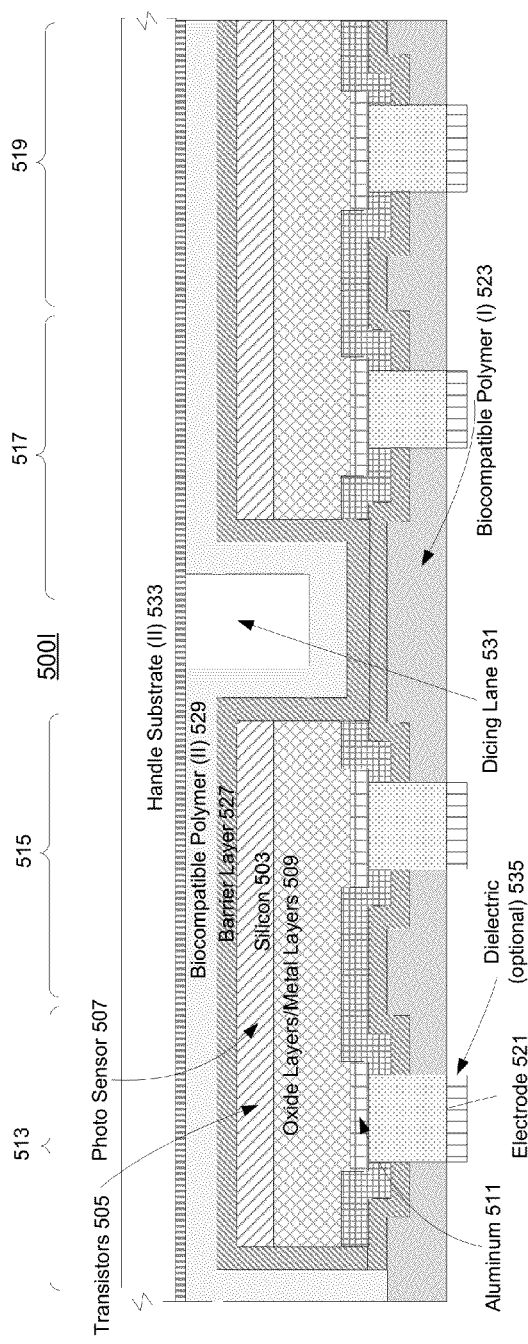
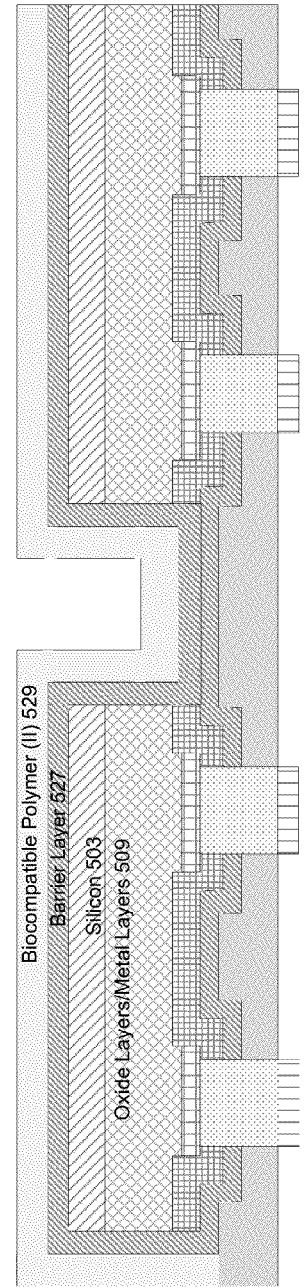
Fig. 5I
Fig. 5J

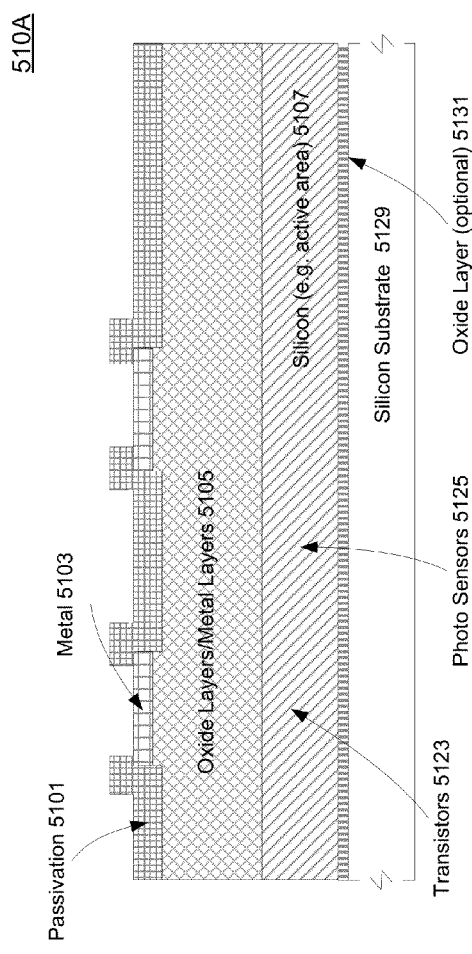
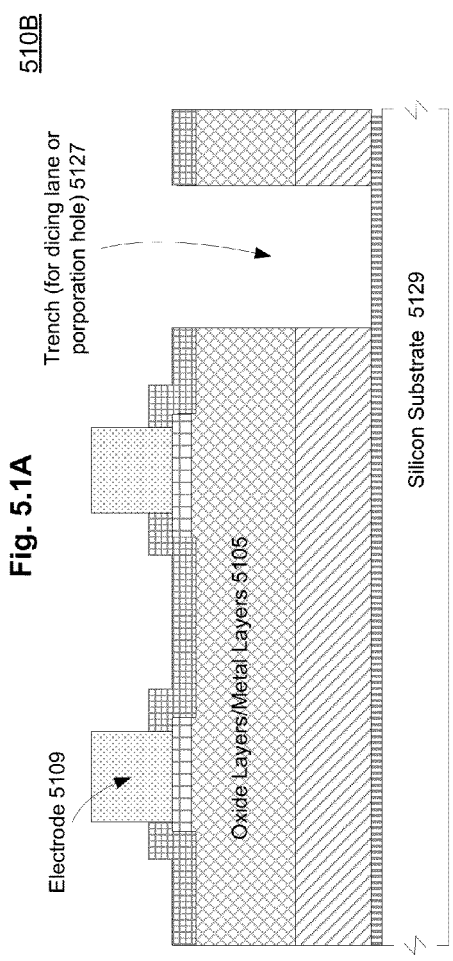
Fig. 5.1A
Fig. 5.1B

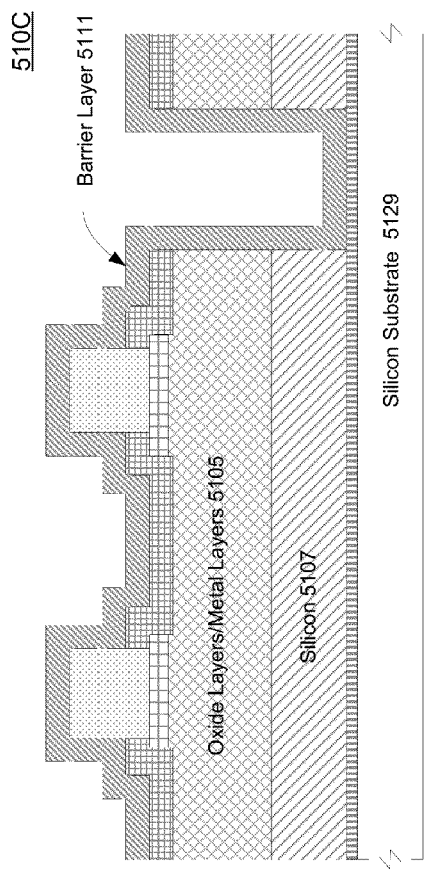
Fig. 5.1C
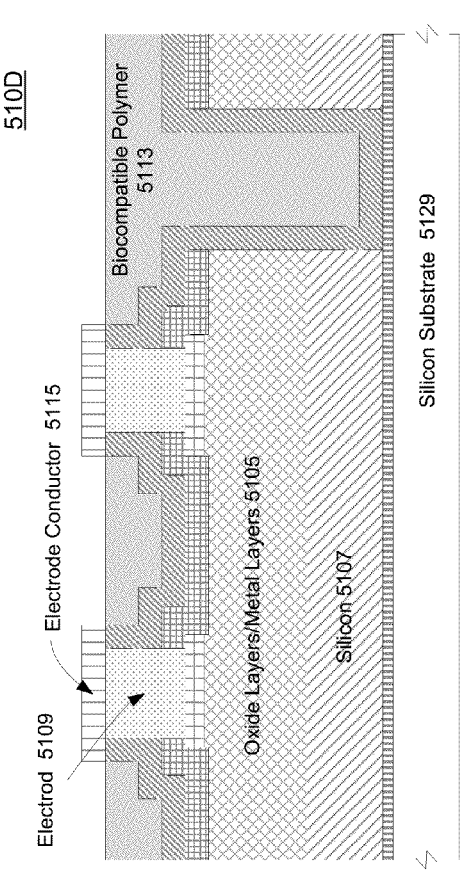
Fig. 5.1D

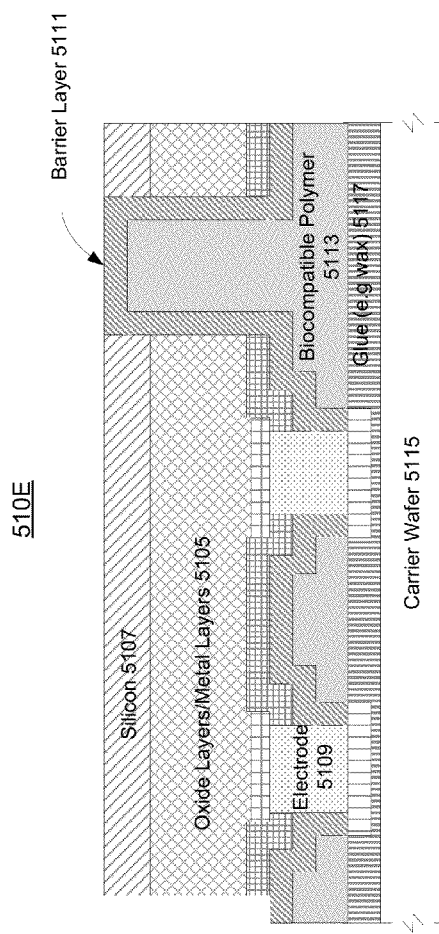
Fig. 5.1E
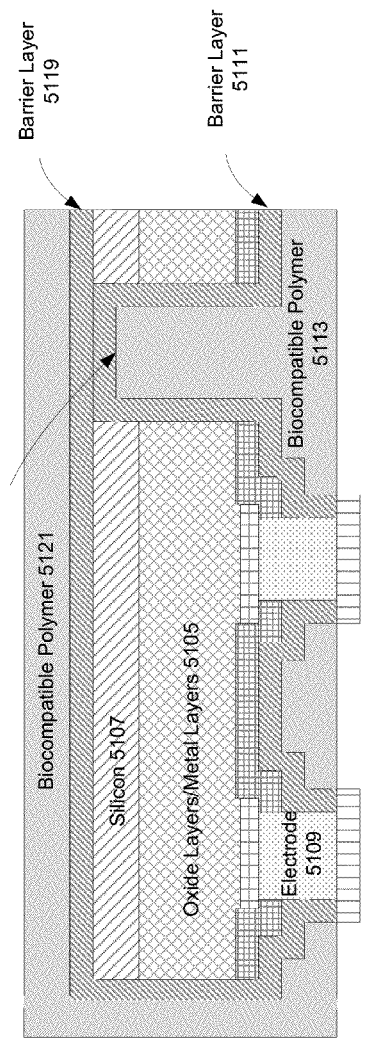
Fig. 5.1F

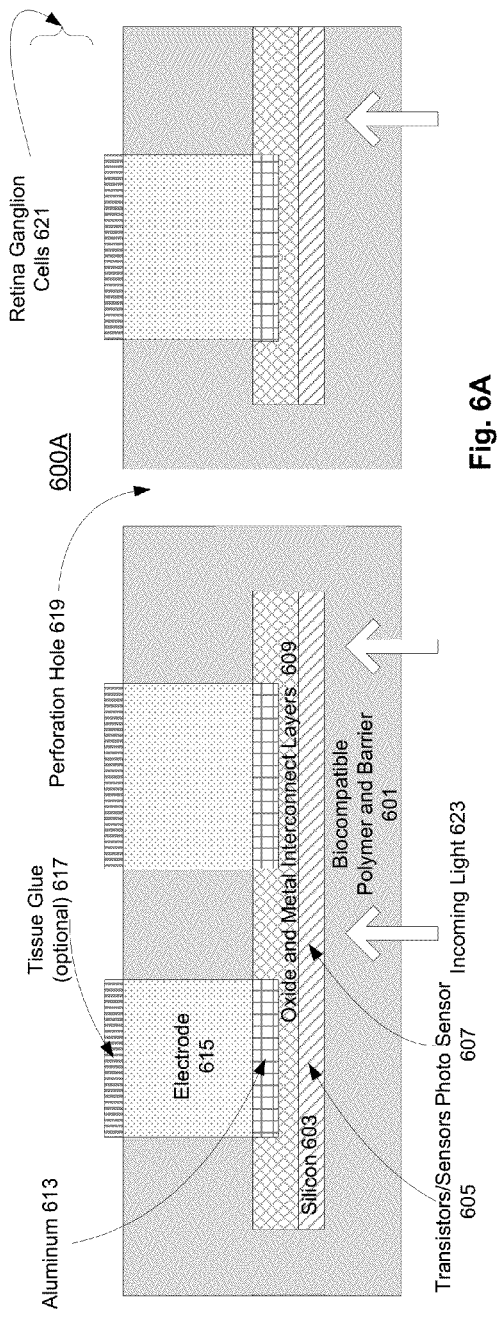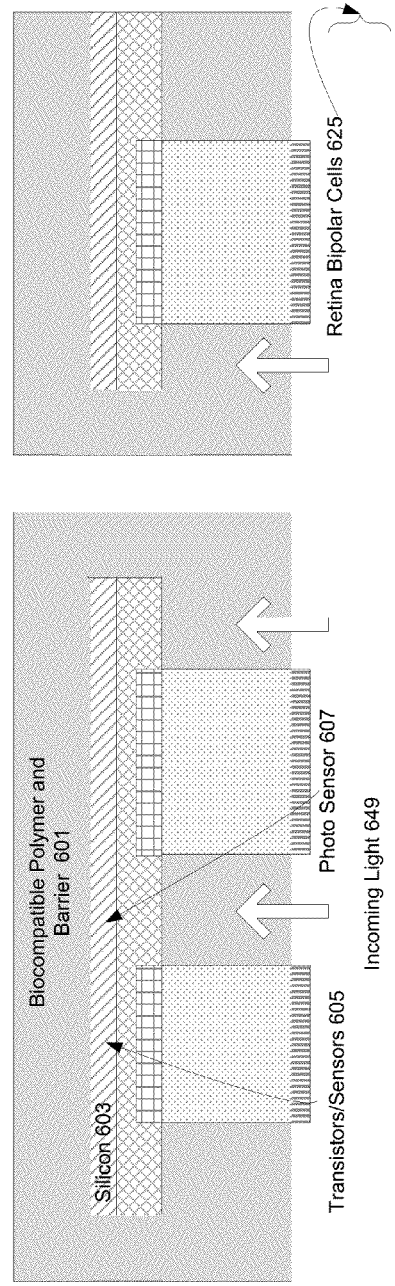
Fig. 6A
Fig. 6B

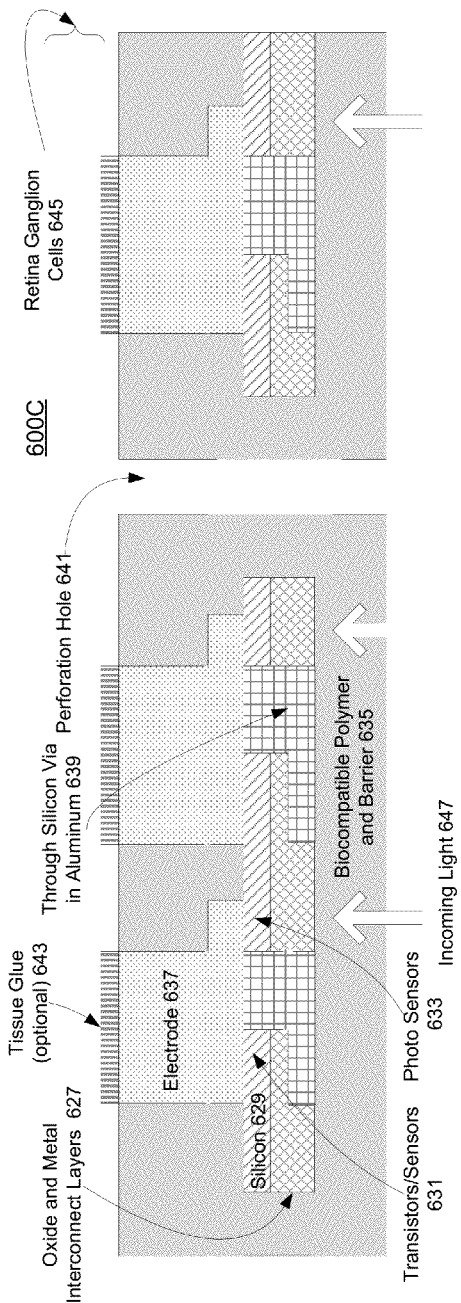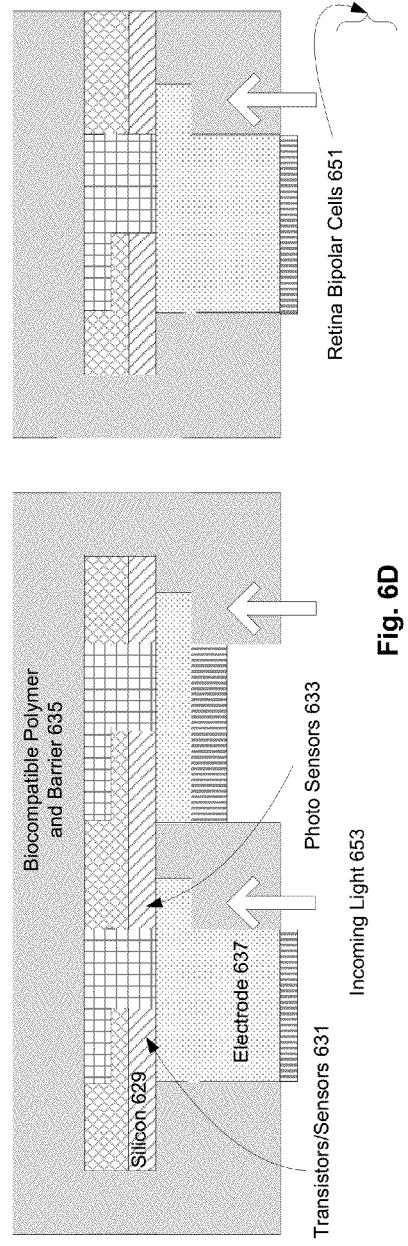
Fig. 6C
Fig. 6D

1300

```
┌─────────────────────────────────────────────────────────────────────┐
│ Detecting predetermined light patterns to cause a device into a     │
│ calibration mode, wherein the device comprises an array of pixel    │
│ units to receive light to enable perception of vision of the light, │
│ and wherein the pixel units are configurable via electrical         │
│ parameters 1301                                                     │
└─────────────────────────────────────────────────────────────────────┘
                                   │
                                   ▼
┌─────────────────────────────────────────────────────────────────────┐
│ Receiving light patterns to select one or more pixel units from the │
│ array, the light patterns associated with known effect of visual    │
│ sensation 1303                                                      │
└─────────────────────────────────────────────────────────────────────┘
                                   │
                                   ▼
┌─────────────────────────────────────────────────────────────────────┐
│ Generating stimuli from the selected pixel units to stimulate       │
│ neuron cells to cause actual effect of visual sensation via the     │
│ light patterns 1305                                                 │
└─────────────────────────────────────────────────────────────────────┘
                                   │
                                   ▼
┌─────────────────────────────────────────────────────────────────────┐
│ In response to receiving external commands, updating the electrical │
│ parameters for the selected pixel units to improve the actual       │
│ effect of visual sensation for the known effect of visual           │
│ sensation 1307                                                      │
└─────────────────────────────────────────────────────────────────────┘
```

Fig. 13

FLEXIBLE ARTIFICIAL RETINA DEVICES

CROSS-REFERENCE TO RELATED APPLICATIONS

The present application is a continuation in part of, and claims the benefit of U.S. patent application Ser. No. 13/102,596, filed on May 6, 2011 entitled "RETINA STIMULATION APPARATUS AND MANUFACTURING METHOD THEREOF" (now abandoned), which claims the benefit of Provisional Patent Application No. 61/407,229, filed on Oct. 27, 2010, entitled "Retina Prosthesis and the Fabrication Methods of Such", both of which are hereby incorporated by reference in its entirety into this application.

FIELD OF INVENTION

The present invention relates generally to micro devices, and more particularly to flexible integrated circuit devices capable of stimulating neural cells.

BACKGROUND

Age-related macular disease (AMD) and the retinitis pigmentosa (RP) disease have been identified as major causes of blindness, especially for senior people worldwide. Retinal prosthesis device offers possible restoration of part of the vision to the blindness. Typically, the device includes micro electrodes requiring separate wiring implant to control each micro electrode. However, field of view provided by such devices, which depends on the number of micro electrodes and pitch of micro electrodes included in the device, may be severely limited because of size limitation on the wiring implant.

Furthermore, the image resolution of a retina prosthesis device may be related to density of micro electrodes in the device. Conventional devices for retina prosthesis may include driving circuit chips separate from electrode or image sensor chips implanted to retina tissues. Thus, the required number of electrical interconnections between the micro electrode chips and the driving circuit chips can increase significantly and impose unnecessary ceilings on achievable number of pixels.

In addition, existing retina prosthesis devices may be based on micro electrodes made of planner chips not conforming to non-planar shapes of retina tissues. As a result, additional interferences among the micro electrodes may occur because of the mismatch in shapes to further limit possible image resolution of the device.

Thus, traditional retina prosthesis devices are inherently limited to provide levels of image resolutions, field of views or other visual characteristics to achieve levels close to a real retina to help patients recover from impaired vision capabilities.

SUMMARY OF THE DESCRIPTION

In one embodiment, a flexible integrated device can provide high resolution of electrical excitations (e.g. down to individual retina cell level) over at least one mm (milli meter) to several mm of retina area corresponding to a few degrees to a few tens of degrees field of view for retina prosthesis. The flexible integrated device may be capable of tuning and calibration for adjusting excitation to target retinal neurons. In one embodiment, the flexible integrated device may be implanted using either an epi-retinal (e.g. from the front side of retina facing the incoming light or on the retina) approach or a sub-retinal (e.g. behind the retina) approach.

In another embodiment, a single flexible CMOS (complementary metal-oxide-semiconductor) chip can integrate an array of pixel units. Each pixel may comprise a micro electrode, photo sensor, signal processor and driver circuitry. The flexible chip can be fabricated thin enough to conform to the shape of a retina. For example, the flexible chip about 3 mm in diameter may be bendable to about 90 µm (micro meter) from the center of the chip to the edge of the chip to form a two dimensional curved surface of a quasi-spherical shape similar to that of a contact lens.

In another embodiment, a flexible integrated device may include a mosaic of sub-modules divided via boundaries. Device material except some conducting lines (e.g. metal lines) between these sub-modules may be removed from the boundaries to increase moldability (e.g. flexibility to conform to different shapes) of the device. In some embodiments, the flexible integrated device may be perforated (e.g. with perforation holes) to maintain some fluidic flow across the device. Optionally or alternatively, the flexible integrated device may include a thin substrate to allow a portion of light to penetrate through the backside of the chip to the integrated photo sensors, and applicable in epi-retinal prosthesis.

In another embodiment, a flexible integrated device may include electrodes fitted with local return paths (or "guard ring") to confine and shorten the total distance of electric flows from the electrodes. As a result, the amount of electricity lost in transit of the electric flows can be lowered to prevent unwanted stimulation of neural cells farther away from the target neuron cells, such as the bipolar cells or ganglion cells in the sub-retina case. The surfaces of electrodes may be positioned in three dimensions manner with multiple electrode heights from the substrate of the device to differentially stimulate different layers of neuron cells, such as strata of ON and OFF cells.

In another embodiment, a flexible integrated device may include on-chip signal processing circuitry capable of generating appropriate stimulus waveforms for a pixel unit by taking inputs from multiple pixel units, such as nearby neighboring pixel units. The flexible integrated device may include electrical sensing circuitry capable of identifying the specific types of target neural cells interfacing to each pixel unit through the receptive field and firing patterns from the target neural cells (e.g. located close to the pixel unit).

In another embodiment, a provision system including a flexible integrated retina chip implanted to a user as retina prosthesis may allow fine tuning of the chip via external commands. For example, each pixel unit in the chip may include specific receivers and/or circuitry for receiving optical and/or wireless communication signals for the external commands to select and/or configure portions of the chip according to the user's visual perception. The provision system may include a remote control to issue the external commands optically or wirelessly.

In another embodiment, an implant apparatus may comprise a plurality of photo sensors to receive light, a plurality of electrodes and circuitry coupled to the photo sensors and the electrodes. The circuit may drive the electrodes to stimulate neuron cells for enabling perception of a vision from the light captured by the photo sensors. The apparatus may be implemented in a flexible material to conform to a shape of a human eye ball to allow the micro electrodes in close proximity to the neuron cells for the stimulation.

In another embodiment, an apparatus implementable to tissues including neuron cells may comprise a plurality pixel units arranged in a two dimensional array to enable perception of a vision from light incoming to the pixel units. Each pixel unit may comprise a photo sensor to receive the light, an electrode to deliver a stimulus to targeted ones of the neuron cells for the perception, and a circuitry to derive the stimulus from the light to drive the electrode. The two dimensional array may be arranged within a device having a front surface and a back surface opposite to the front surface. Biocompatible layers may wrap the device to bi-directionally protect the device and the tissues. In one embodiment, the biocompatible layer may include openings to allow electrodes of the pixel units to stimulate the neuron cells. The device may comprise flexible material to allow the device to be bendable to conform to the shape of a human eye ball. The flexible material may be translucent to enable the device to receive the light from either the front surface or the back surface of the device.

In another embodiment, an integrated circuit device for retina prosthesis may comprise an array of pixel units to enable perception of a vision of light. Each pixel unit may comprise a sensor to sense the light, a micro electrode to deliver a stimulus to targeted ones of neuron cells for the perception and a circuitry to derive the stimulus from the light to drive the electrode. The array of pixel units may be arranged with a density of higher than 1000 per square millimeter in the device. In one embodiment, the device may be flexible to allow the array of pixel units to conform to a radius of curvature of at least 12.5 millimeter according to a shape of a human eyeball.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate similar elements and in which:

FIGS. 1A-1B are block diagrams illustrating embodiments of integrated flexible devices for retina prosthesis;

FIGS. 4A-4B are block diagrams illustrating cross sectional views of flexible devices in one embodiment of the present invention;

FIGS. 5A-5J are block diagrams illustrating a sequence of fabrication processes for flexible devices in one embodiment of the present invention;

FIGS. 5.1A-5.1F are block diagrams illustrating an alternative or preferred sequence of fabrication processes for flexible devices in one embodiment of the present invention;

FIGS. 6A-6D are block diagrams illustrating exemplary layered structures of flexible devices for different approaches to implant retina prosthesis;

FIG. 13 is a flow diagram illustrating a method to configure flexible devices in one embodiment described herein.

DETAILED DESCRIPTION

Figure 2A:
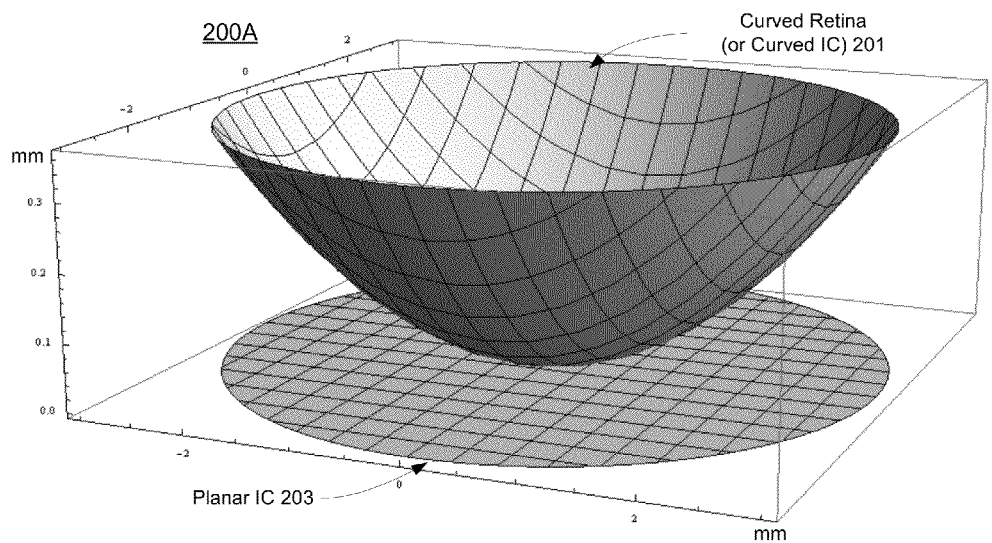
FIGS. 2A-2B are relationship diagrams illustrating effects of flexible devices which are curved according to one embodiment of the present invention.

Flexible artificial retina devices are described herein. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

A flexible IC (integrated circuit) device can integrate an array of "pixels" in a sing chip. Each pixel can comprise an electrode, sensors (e.g. photo sensors, electric sensors or other applicable sensors), a signal processor and/or driver circuitry. The integration can simplify wiring, fan out, multiplexing or other requirements to enable intended functions of the device. Costly signal transmission, for example, via EM (electromagnetic) waves, between sensor/processing circuitry and electrode arrays may be eliminated. Each pixel can be accessible within the device to allow thousands or tens of thousands of pixels in the device to interface with neuron cells. For example, the flexible integrated device may provide required density to restore a 20/80 visual acuity corresponding to about a two to four mm-sized, high density array with 10,000-20,000 pixel units.

In one embodiment, flexibility of an integrated device may be based on controlled thickness of the device. For example, the device can be thin enough to bend ~90 μm from the center to the edge to conform to the shape of a retina (e.g. a human eye ball). In some embodiments, the device may be made (e.g. according to a fabrication process) thin enough to be bent to a radius of curvature smaller than 12 mm, about the average radius curvature of a human retina, still within the safety margin of the material strength of the device.

As a device is bendable to conform to the curvature of a retina, the neuron-to-electrode distance between electrodes of the device and target neuron cells of the retina can be reduced. Consequently, the power required in each pixel to excite or stimulate the neuron cells can be reduced to enable a higher pixel density with the allowed power density given and improve resolution of images perceived via the neuron cells using the device implanted to a patient. In certain embodiments, the device can meet the conformity requirements for exciting individual retinal neuron (e.g. targeting an individual neuron cell per electrode).

In one embodiment, a flexible integrated circuit (or device) for retina prosthesis may be fabricated based on an 180 nm (nanometer) CMOS technology using <~30 micrometer thick Si device layer sandwiched between two biocompatible polymer and barrier layers (such as Polyimide/SiC, Parylene/SiC). Both biocompatible polymer (such as polyimide, parylene, liquid-crystal polymers etc.) and barrier layer (such as SiC, TiN, DLC diamond-like carbon or diamond films etc.) may be compatible (e.g. biocompatible) with ISO (International Organization for Standardization) 10993 standards to provide bi-directional protection (e.g. to allow long-term contact) between the flexible integrated device and surrounding tissues when the device is implanted within the tissues.

The fabrication approach of a flexible integrated device may enable integration of high density CMOS image sensors and signal processing circuitry together with neuron stimulating electrode arrays on the same flexible patch needed for medical implants. In some embodiments, semiconductor substrate may be used in the device to allow inclusion of necessary optical and/or electronic components for sensing optical images and producing electrical stimulus as a function of the sensed optical images.

In an alternative embodiment, a flexible integrated device may be applicable in different manners of retina implantation. For example, the device may be manufactured to be thin enough to allow certain portion of light to pass through the device. Sensors and electrodes may be positioned in the same side (or surface) or opposing sides of such a translucent device. As a result, the device may be implanted in an epi-retina manner to stimulate retinal ganglion cells (RGC) directly via electrodes of the device without utilizing a retinal neural network before the RGC layer. Alternatively, the device may be implanted in a sub-retinal manner to stimulate the retina from the bipolar cell side via the electrodes, for example, to work together with the remaining neural network formed by a variety of neuron cells, such as bipolar cells, horizontal cells, amacrine cells etc.

In one embodiment, a flexible integrated device may be capable of exciting target neuron cells or nerves according to characteristics of the neuron cells responding to light stimuli. For example, the characteristics may indicate the target neuron cells are ON type cells, OFF type cells or other types of cells. An ON type cell may respond substantially synchronous with onset of light stimuli. An OFF type cell may respond substantially synchronous with offset of the light stimuli. The flexible integrated device may include processing capability to generate stimuli from received light to properly excite the targeted neuron cells (e.g. as if the neuron cells are directly stimulated by the received light), for example, via special stimulation pattern (or waveforms), time delays, ignition, suppression, or other applicable stimulation manners, etc. In one embodiment, the flexible integrated device may include multiple layers of electrodes (e.g. distributed in a three dimensional manner) to allow physical selection (e.g. based on proximity) of different layers of neuron cells (e.g. due to neuron connection stratification) to communicate (or stimulate). For example, each electrode or micro electrode may be positioned to target a small number (e.g. limited to be smaller than a predetermined number, such as 4, 8, or other applicable number) of neuron cells without affecting other neuron cells not targeted.

A flexible integrated device may be configurable to provide customized functionalities for different retina implant needs. For example, manual and/or self (automatic) calibration operations may be applied in vitro (e.g. subsequent to implantation into a patient) to identify types of targeted neuron cells and/or adjusting sensor/electrode array parameters of the device according to actual visual perception of the receiving patient. Processing functions may be activated or programmed (e.g. through programmable circuitry) to provide equivalent signal processing effects, for example, to replace damaged neuron cell networks to improve impaired vision of the receiving patient.

FIGS. 1A-1B are block diagrams illustrating embodiments of integrated flexible devices for retina prosthesis. Device 100A of FIG. 1 may include a two dimensional array of pixel units. Each pixel unit may include similar structures. For example, pixel unit 107 may comprise a photo sensor 101 to receive incoming light, processing circuitry 105 to perform operations, and electrode 103 to stimulate target neuron cells to allow perception of vision projected by the incoming light. In one embodiment, processing circuitry 105 may include digital, analog or other applicable circuits to process sensed light from photo sensor 101 for generating a stimulus or waveform, activation patterns, etc. to drive electrode 103 to stimulate the targeted neuron cells.

Alternatively, device 100B of FIG. 1B may include pixel unit 109 comprising photo sensor 111, electrode 113 and circuitry 115. Electrode 113 may interface with target neuron cells to deliver stimulus to and/or sense electric activities from targeted neuron cells. The stimulus may be derived from light captured by photo sensor 111. In one embodiment, circuitry 115 may provide processing (e.g. signal processing) functions for receiving, processing, and/or driving electric signals. For example, electric signals may be received via sensed light from photo sensor 111 or sensed electrical fields from electrode 113. Circuitry 115 may drive stimulus as electric signals via electrode 113.

The incorporation of electrical sensing circuit 115 in the retinal prosthesis chip device 100B may enable automatic or manual identification of neuron cells through sensed receptive field (e.g. electrical field) and neuron spiking patterns in time domain. Examples may be functional asymmetries in ON and OFF ganglion cells of primate retina that receptive fields of ON cells is 20% larger than those of OFF cells, resulting in higher full-field sensitivity, and that On cells have ~20% faster response kinetics than OFF cells. A large array of cell-sized micro electrodes conforming to the retina and capable of both sensing and stimulating may allow selective stimulating or suppress ON and OFF retina retinal ganglion cells.

Figure 2B:
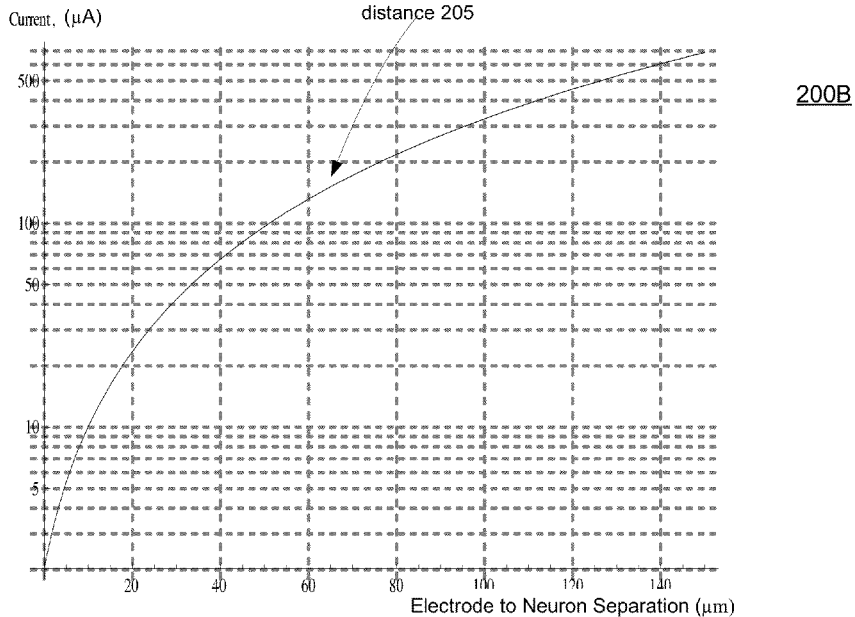

FIGS. 2A-2B are relationship diagrams illustrating effects of flexible devices which are curved according to one embodiment of the present invention. Typically, image resolution and required driving power (e.g. threshold current density) of a retina prosthesis device may depend on curvature of the device. In one embodiment, a flexible integrated device for retina prosthesis may include cell-pitched electrode array (e.g. each electrode is about the size of a single neuron cell) fabricated by planar IC lithography technology. FIG. 2A shows distribution diagram 200A of neuron-to-electrode distances for implementing an mm-sized planner electrode array chip in contact with a retina curved according to a human eye ball, which is roughly spherical with an average diameter of 25 mm.

As shown in distribution diagram 200A, an mm-sized planar electrode array chip 203 in contact with the retina 201 at the chip center may quickly separate from the retina by about 90 microns at distance 1.5 mm from the center toward the edge of the chip. This increase of neuron-to-electrode distance can imply, for example, increase in the threshold current needed for an electrode to depolarize target neurons. As shown in relationship diagram 200B of FIG. 2B, the increase in the threshold current required can be 1-2 orders in magnitude larger than that in close proximity according to curve 205. Additionally, the increase of neuron-to-electrode distance may reduce the resolution to depolarize particular neurons since the field lines and electrical currents (e.g. for sending stimulus signals) from the electrodes may spread out with distance and cover a large area to reach distant neurons. In one embodiment, a flexible integrated device of the present invention may be implanted without the large distance or separate implications shown in FIGS. 2A and 2B.

Figure 3:
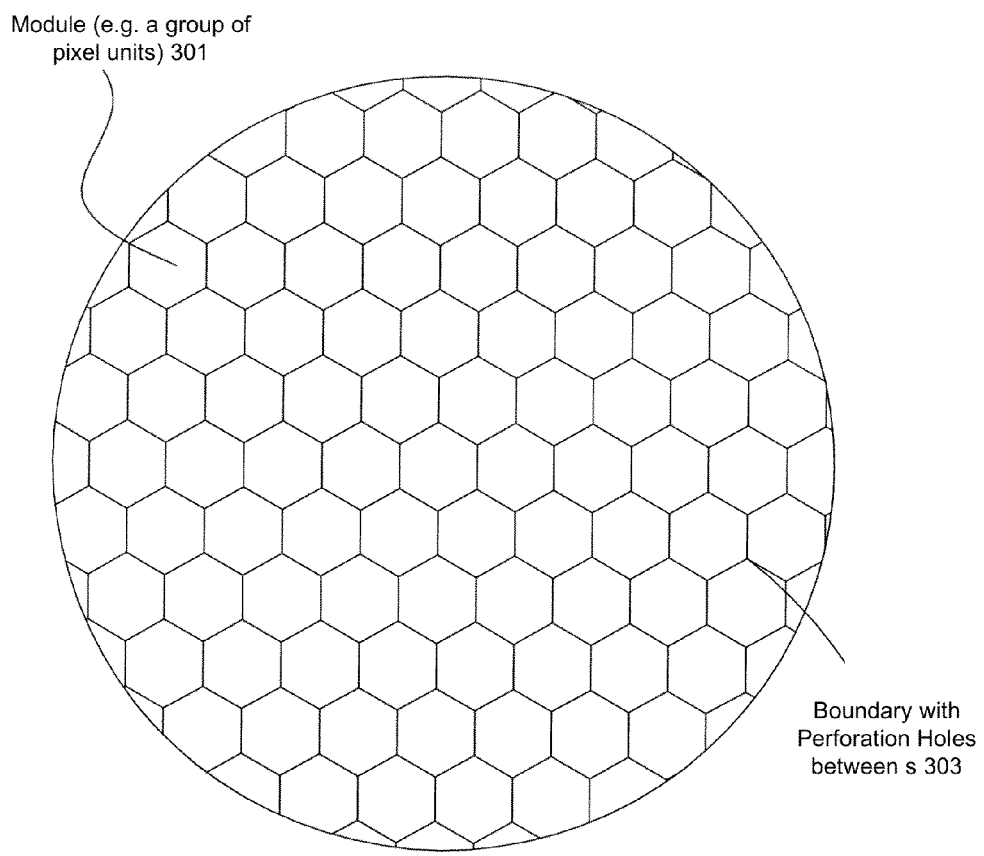
FIG. 3 is a schematic diagram illustrating an exemplary device with perforation holes according to one embodiment of the present invention.

FIG. 3 is a schematic diagram illustrating an exemplary device with perforation holes according to one embodiment of the present invention. Device 300 may be flexible in multiple dimensions to curve with at least about a curvature of average human eye ball (e.g. 25 mm in diameter). In one embodiment, device 300 may include multiple hexagonally packed modules with boundaries between adjacent modules perforated with perforation holes.

Each module, such as module 301, may include a group of pixel units in a partition of a device. The partition may be fabricated in a hexagonal shape, rectangular shape, or other applicable shapes. In one embodiment, perforation holes may allow fluid to exchange between different surfaces of device 300. Boundaries between adjacent modules, such as boundary 303 may include metal trace (or other conductive trace or conductive lines) as signal lines for the adjacent modules to directly communicate with each other. Metal traces may provide power distribution among the modules. Perforation can maintain some fluidic flow between tissues of both sides of the device (e.g. implanted within the tissues) through the perforation holes. The complete removal of integrated circuit material (e.g. silicon) between the polymer and barrier layers except metal lines along the boundaries can increase the moldability of the device.

FIGS. 4A-4B are block diagrams illustrating cross sectional views of flexible devices in one embodiment of the present invention. Cross section 400A of FIG. 4A may indicate a flexible integrated device having multiple pixel units 417, 419, 421, 425 with layered structures, such as silicon layer 407, oxide and metal interconnect layers 409 or biocompatible layers including polymer 401 and barrier layer. Unit 417 may include transistors 403, photo sensor 405 in silicon layer 407 and electrode 413 coupled with circuitry (e.g. including transistors 403) via aluminum 411. Perforation hole 403 may be formed across the device along a boundary between adjacent modules. For example, units 417, 419 may be grouped in one module adjacent to a separate module including units 421, 425.

Cross section 400B may indicate a cross sectional view between adjacent modules (or pixel units) of a flexible integrated device with a cutting plane across a boundary of the modules without cutting through perforation holes. Passivated metal lines or other flexible, conductive lines, such as metal wire 423, can run across the boundary (e.g. between the perforations holes) to bring electrical signals from unit to unit.

FIGS. 5A-5J are block diagrams illustrating a sequence of fabrication processes for flexible devices in one embodiment of the present invention. In one embodiment, CMOS and integration of photo sensors with electrode arrays in structure 500A of FIG. 5A may be fabricated using a standard or slightly modified CMOS technology or a CMOS image sensor (CIS) technology on silicon wafer. Preferably, the silicon wafer may comprise an SOI (Silicon On Insulator) wafer with a silicon epitaxial layer a few micrometers in thickness. A PN junction diode may be used via the modified CMOS technology as a photo sensor. Alternatively, photo sensors with optimized doping profiles and anti-reflection coatings may be used via the CIS technology. In certain embodiments, CMOS-compatible conducting films such as TiN might be deposited on top of electrode layers (e.g. aluminum 511) before patterning electrodes. The electrodes may be exposed in the final pad opening step of a conventional CMOS process.

In one embodiment, structure 500A of FIG. 5A may comprise layered structures for a flexible integrated device including transistors 505, photo sensor 507, aluminum 511 for pixel unit 513 over silicon layer (or semiconductor layer) 503, oxide/metal layers 509, Si substrate 501 and optional oxide layer 541. Structure 500A may include pixel units 515, 517, 519 having similar components as in pixel unit 513. Structure 500A may have a front side (or front surface, transistor side) 537 and a back side 535 opposite to the front side 537. Structure 500A may include passivation layer 539 as a result of, for example, a CMOS process. Front side 537 may correspond to the chip surface of a wafer or a silicon chip.

Subsequently, as shown in FIG. 5B, the front surface of a layered structure may be further passivated by adhesion/barrier thin films (e.g. about 0.1 µm to a few tm in thickness) based on, for example, SiC, diamond or DLC (Diamond-Like-Carbon) material or layers. In one embodiment, structure 500B of FIG. 5B may include barrier layer 525 as a result of the passivation. The adhesive/barrier thin films may cover already opened pad and electrode areas for a flexible integrated device, for example, at the final step of a CMOS process.

After the passivation process, pad and electrode areas may be reopened by photolithography and etching with a slightly smaller window sizes than the original window sizes, which are smaller than the pad size and electrode size made in the CMOS process. As a result, the exposed side walls surround the pads and electrodes may be protected by the adhesive/barrier layer deposited during the passivation process. The exposed side walls, if not protected or covered, may expose materials of the standard CMOS passivation layers such as PECVD (Plasma-Enhanced Chemical Vapor Deposition) silicon dioxides and silicon nitrides.

In one embodiment, a metal electrode, such as aluminum 511, may be applicable for an electrode. A biocompatible polymer deposition, such as biocompatible polymer (I) 523, may be applied over a barrier layer, such as barrier layer 525. The biocompatible polymer may be based on Polyimide, PDMS (Polydimethylsiloxane), Parylene, liquid-crystal polymer or other applicable biocompatible material. In one embodiment, the biocompatible material may be selected according to standards specified via ISO 10993 standard. After applying the biocompatible layer, in one embodiment, a first handle wafer may be bonded to the front side of the device wafer. For example, structure 500C may include handle substrate (I) 543 bonded via glue 545 in FIG. 5C. Structure 500C may be ready for thinning treatment from the backside. In some embodiments, electrodes can be opened right after the biocompatible polymer layer, such as biocompatible polymer (I) 523, is deposited.

Turning now to FIG. 5D, silicon substrate of a device wafer, such as substrate 501 of FIG. 5C, can by thinned down to a proper thickness by a combination of lapping and chemical etching steps. After bonding to the carrier substrate, such as handle substrate (I) 543 of FIG. 5C, the Si wafer substrate, such as substrate 501, may then be mechanically thinned to a thickness of about 50 micrometers or other proper thickness size by a wafer lapping machine. The resulting surface may include micro-crack damages induced during the lapping process. In one embodiment, a silicon chemical etching process, such as SF6 plasma etching, dry XeF2 etching, or other applicable etching processes, may be applied to a controlled thickness to remove these damages. Alternatively, etching over a substrate using SOI may stop at the buried oxide layer as etching stop. Typically, the thickness may be controlled to be from several microns to less than several tens of microns such that the photo sensors can effectively absorb photons through the thickness and the substrate is still bendable to the desirable curvature. Structure 500D of FIG. 5D may include a wafer substrate which has been substantially thinned down via the thinning process.

Turning now to FIG. 5E, adhesion/barrier thin films may be deposited on a polished and/or etched surface after the thinning process. Trenches for dicing lanes (or perforation holes), such as dicing lane 531 may be formed. Barrier layer 527 may be deposited over the backside of structure 500E of FIG. 5E. Subsequently, perforation holes (or via holes) between device front and back surfaces may be patterned and opened by, for example, lithography and RIE (Reactive Ion Etching) processes or other applicable processes. For example, structure 500F of FIG. 5F may include perforation hole or dicing lane 531. In some embodiment, edges of a flexible device may be similarly opened as shown in open 539 of FIG. 5F.

Turning now to FIG. 5G, a polymer layer may be further etched through to a handle substrate for perforation holes. For example, structure 500G may include perforation hole 531 etched through biocompatible polymer (I) 523 to handle substrate (I) 543. Subsequently, a second biocompatible polymer layer may be deposited and patterned to open up the perforation holes. For example, biocompatible polymer (II) 529 may be deposited over the backside of structure 500G and opened for perforation hole 531. Two biocompatible layers may seal together to wrap around a device as similarly shown in seal 535 of FIG. 5G. In one embodiment, biocompatible polymer 529 (e.g. 10 μm thick) may be thicker than barrier layer 527 (e.g. about 1 or 2 μm thick). Biocompatible polymers 529, 523 may be of a similar size of thickness.

Subsequently, a second handle substrate may be bonded to a device on the opposite side of a first handle substrate, which has already been boned to the device. The first handle substrate may be removed from the device. For example, structure 500H of FIG. 5H may include a newly bonded handle substrate (II) 533 over the back side with the first handle substrate, such as handle substrate (I) 543, removed from the front side.

After removing a handle substrate from the front surface, electrodes may be exposed by applying lithography and RIE (Reactive Ion Etching) process or other applicable processes. For example, structure 500I of FIG. 5I may include an opening through biocompatible polymer (I) 523 for electrode 521 on the front side. Electrode 521 may comprise conductive metallic material such as gold, platinum and/or copper. In one embodiment, electrode 521 may be covered by another layer of metallization (IrOx, Pt, TiN, FeOx etc.) for a better electrode-to-electrolyte interface. Alternatively or optionally, an electrode may include an optional dielectric layer (e.g. a thin layer of high-k dielectrics of about 0.1 μm), such as dielectric 535 of FIG. 5I, for providing stimulation based on displacement current instead of direct current. In some embodiments, another optional adhesive layer, such as about a few micron to less than 0.1 μm of laminin, may be deposited on the top surface of the electrode (or a flexible device) to help the electrode (or the flexible device) to adhere to tissues for improving implantation. Finally, a second handle wafer may be removed to complete the fabrication process of a flexible integrated device. For example, structure 500J of FIG. 5J may represent a flexible integrated device without a second handle substrate, such as handle substrate (II) 533 of FIG. 5I.

FIGS. 5.1A-5.1F are block diagrams illustrating an alternative or preferred sequence of fabrication processes for flexible devices in one embodiment of the present invention. CMOS circuits and integration of photo sensors with micro electrode arrays in structure 5100A of FIG. 5.1A may be fabricated using a standard or slightly modified CMOS/CIS technology or other applicable technologies on a silicon wafer. Trenches for dicing lanes (e.g. about 50~100 μm wide) and optional perforation holes may be processed based on front side processing without requiring more than one carrier handler to fabricate the flexible devices. As a result, the manufacturing procedure may be streamlined as the thinning process (e.g. backside lapping) may be considered a dirty process and restricted from sending back to certain clean fabrication processes.

In one embodiment, structure 510A may include oxide/metal layer 5105 and active silicon layer 5107 over a silicon or SOI wafer (not shown in the figures) according to, for example, a CMOS/CIS process. The active silicon layer 5107 may include transistors 5123 and photo sensors 5125 over silicon substrate 5129 with an optional oxide layer 5131 in between silicon layers 5107 and 5129. At the end of a CMOS/CIS process, structure 510A may include passivation 5101 (e.g. silicon nitride/oxide) with metal contact pads, micro electrodes opened, such as metal 5103.

Turning now to structure FIG. 5.1B, structure 510B may include electrodes 5109 and trenches 5127 for dicing lanes or perforation holes for flexible devices may be fabricated from structure 510A. For example, thin metal films may be added to cover the wafer of structure 510A. A thick photo resistance material may be added by spin coating the wafer on the thin metal films. Electrode 5109 may be added via electroplating (e.g. including Pt or Au material) after the thick-photoresist photolithography processes. Subsequently, the photo resistance material and the thin metal film may be removed. In one embodiment, electrode 5109 may be about the same thickness of the desired thickness of the final covering polymer layer (for example, 10 μm). Additional photo resistance coating and photolithography exposure may be applied to the surface and an RIE processes are used to etch through the passivation layer, the silicon dioxide layers, and into the silicon substrate to create trench 5127. Trench 5127 may be etched through the silicon area (or active silicon layer) 5107.

Subsequently, turning now to FIG. 5.1C, structure 510C may include a barrier layer 5111 deposited over structure 510B of FIG. 5.1B. Barrier layer 5111 may be based on DLC (diamond like carbon), SiC or other applicable material. Fabrication to add barrier layer after forming the electrode 5109 may ensure protection of electrode 5109 sidewalls surrounded or enclosed by the barrier layer. Biocompatible polymer layer may then be coated to cover barrier layer 5111. For example, structure 510D of FIG. 5.1D may include biocompatible polymer 5113. In one embodiment, a polymer layer of about 20 μm thick may be applied via spin-coat and followed by curing processes. The polymer layer may be planarized via lapping process or reactive ion etching process to close to the electrode thickness (for example, about 10 μm thick).

Structure 510E may include electrode conductor 5115 based on SIROF (sputtered iridium oxide film). In one embodiment, SIROF may be deposited via sputtering iridium target in oxygen-containing plasma, and using a lift-off process to define the electrode region. Finally, an optional thin dielectrics layer maybe deposited on top of the microelectrode for a voltage-mode operation of the micro electrodes.

Turning now to FIG. 5.1E, structure 510E include structure 510D of FIG. 5.1D attached to carrier wafer 5115 on the front side by a glue layer (e.g. wax) 5117. Back-side Si substrate (e.g. silicon substrate 5129 of FIG. 5.1D) may be thinned via lapping, chemical etching processes stopping at total thickness of about 20 µm (e.g. stopping at barrier layer 5111 or the buried oxide layer if an SOI wafer is used). Subsequently, a barrier layer may be added on top of already thinned-downed structure 510E followed by another biocompatible polymer coating.

For example, turning now to FIG. 5.1F, structure 510F may include barrier layer 5119 and biocompatible polymer 5121, for example, coated over structure 510E of FIG. 5.1E, based on back-side passivation. Structure 510F may be released from carrier wafer 5115 by dissolving the glue layer 5117. As a result, one layer of barrier layer, e.g. barrier layer 5119, may be deposited in contact of another layer of barrier layer, e.g. barrier layer 5111. Together with the two layers of biocompatible polymer, e.g. polymer 5121, 5113, they may completely cover/enclose the thin chip except in the microelectrode region.

In one embodiment, die separation (or dicing) may be applied via razor blade cutting through dicing lanes, such as over trench 5127. Alternatively or optionally, perforation holes may be created by applying additional photolithography and plasma etching and reactive ion etching processes to remove polymer and barrier layers through trench 5127. An optional adhesive layer (for example, laminin or fibronectin) maybe applied on the micro electrodes surface to promote the contact of tissue to the micro electrodes.

FIGS. 6A-6D are block diagrams illustrating exemplary layered structures of flexible devices for different approaches to implant retina prosthesis. In one embodiment, a flexible integrated device for retina prosthesis can include a thin substrate to allow a portion of light to penetrate through the device (or chip) when not obstructed by metals. Thus, the monolithic chip can to be used for epi-retinal prosthesis even when the photo sensors and electrodes are both fabricated on the front side of the chip.

For example, device 600A of FIG. 6A may include photo sensor 607 and electrode 615 fabricated on the front side (or transistor side) of the device. Device 600A may be implanted in an epi-retinal manner with light 623 coming from the back side of the device. In one embodiment, electrodes and photo sensors of device 600A may face the side towards retina ganglion cells 621. Device 600A may include layered structures including silicon 603 having transistors/sensors 605, oxide layers 609, aluminum 613 and optional tissue glue (for example, laminin, fibronectin etc.) 617 for electrode 615, biocompatible polymer 601 wrapping the device and optional perforation hole 619 opened through the device.

In one embodiment, device 600A may include thin silicon substrate about less than 10 micrometers to allow more than a few percents of light coming from the back side of the device to reach the photo sensors as optical decay length of visible light may be a few microns in silicon. Thin silicon substrate may be based on fabrication processes using SOI (silicon on insulator) wafers and thinning a silicon wafer down after the MOS process.

Turning now to FIG. 6B, device 600B may include similar layered structures as in device 600A of FIG. 6A. In one embodiment, device 600B may be implanted in a sub-retinal manner with light 649 coming from the front side of the device. Electrodes and photo sensors of device 600B may face the side towards retina bipolar cells 625 and incoming light.

In an alternative embodiment as shown in FIG. 6C, device 600C may include photo sensor 633 on the front side and electrode 637 on the back side of the device. Advantageously, electrodes in device 600C will not block incoming light to photo sensors. In one embodiment, device 600C may be implanted in an epi retina manner with light 647 coming from the front side and electrodes facing retina ganglion cells 645 on the back side. Device 600C may include layered structures having silicon 629 with transistors/sensors 631, oxide and metal interconnect layers 627, optional tissue glue 643 for electrode 637, biocompatible polymer and barrier layers 635 wrapping the device and perforation hole 641 across the front and back surfaces of the device. Electrode 637 may be coupled with processing circuitry including, for example, transistors circuit 631, through the conducting vias, such as TSV (through silicon via) in aluminum 639.

Alternatively, in FIG. 6D, device 600D may include similar layered structures as in device 600C of FIG. 6C. Device 600D may be implanted in a sub-retinal manner with light 653 coming from the back side of the device. Electrodes of device 600D may face the side towards retina bipolar cells 651.

Figure 7A:
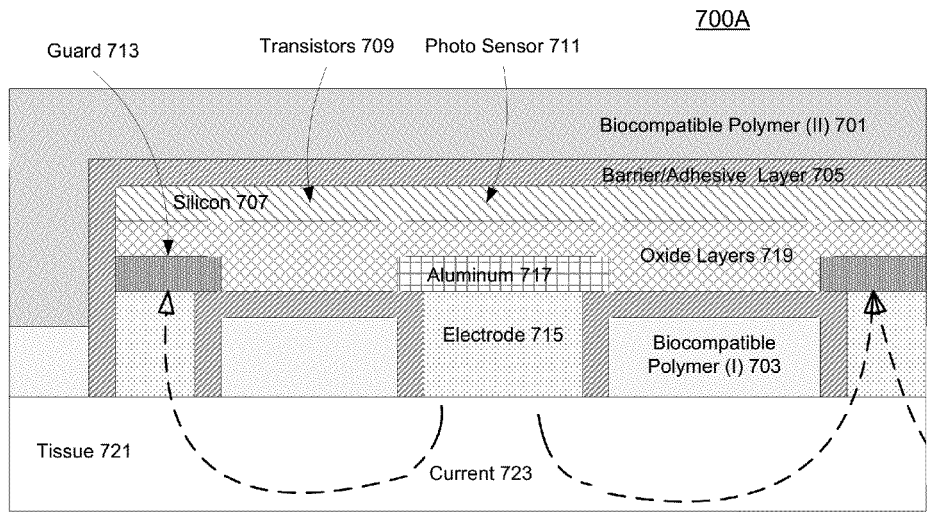
FIGS. 7A-7B are block diagrams illustrating guard rings to provide near-by return path and confine electric flows in exemplary embodiments of the present invention.
Figure 7B:
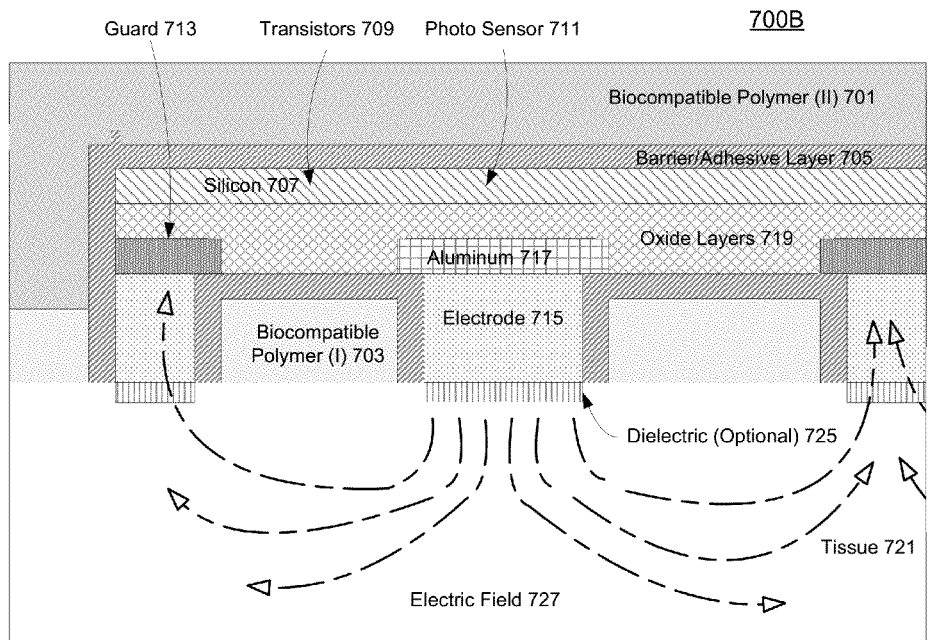

FIGS. 7A-7B are block diagrams illustrating guard rings to provide nearby return path and confine electric flows in exemplary embodiments of the present invention. Device 700A of FIG. 7A may include electrodes fitted with local return paths, or "guard ring" to confine electric flow from the electrodes. In one embodiment, device 700A may be an flexible integrated device with layered structures including silicon 707 having transistors circuit 709 and photo sensor 711, oxide layers 719, electrode 715 over aluminum 717, and biocompatible polymer layers 701, 703 wrapping around the device over barrier/adhesive layer 705. Device 700A may be implanted within tissue 721 in a current driving mode. For example, current 723 from electrode 715 may follow the lowest impedance path. Device 700A may include guard 713 as guard ring (or local return electrode) to provide a local return path guiding current 723 from undesired target directions.

Similarly in FIG. 7B, device 700B may operate in a voltage driving mode with electric field 727 from electrode 715 confined via guard 713. Device 700B may include optional dielectric 725 for electrode 715.

Preferably, electric fields or electrical currents can be confined (or made smaller, narrower) locally close to originating electrodes through guard rings. Thus, unwanted stimulation of neural cells other than target neurons of each electrode, such as stimulating the bipolar cells without exciting the ganglion cells, may be prevented. In a flexible integrated device with guard rings, the electro fields from one electrode may not interfere with other electro fields from separate electrodes using guard rings.

Figure 8:
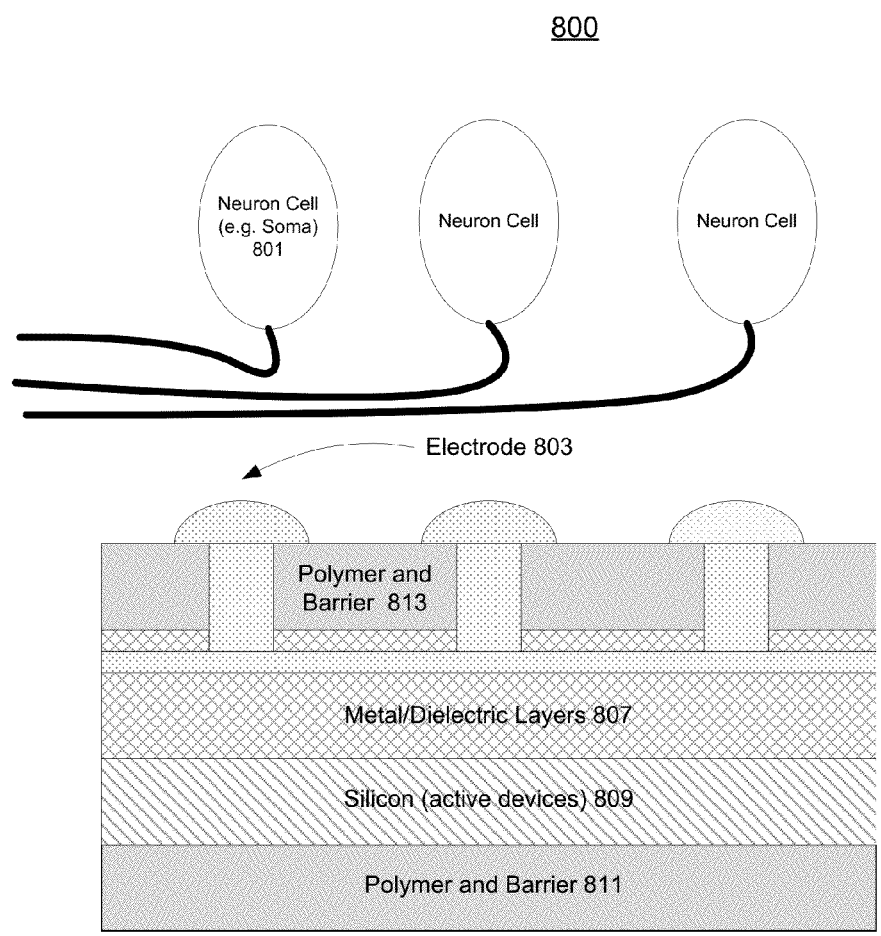
FIG. 8 is a block diagram illustrating layered structures for flexible devices with protruding electrodes in one embodiment of the present invention.

FIG. 8 is a block diagram illustrating layered structures for flexible devices with protruding electrodes in one embodiment of the present invention. For example, device 800 may comprise flexible and integrated chip with protruding electrode arrays. Device 800 may include layered structures having metal/dielectric layers 807, silicon with active components 809, and polymer and barrier layers 811 wrapping the device with the polymer and barrier layers 813. Electrode 803 may be elevated with a protruding tip in close proximity with target neuron cell 801. Preferably, when implanted, elevated stimulus electrodes can push through some of separation layers of tissues to be in closer proximity to the target locations of stimulation. Thus, the required threshold current or power to depolarize the target neurons may be reduced to enable higher number of electrodes with finer resolution (e.g. higher than, for example, at least 250 per square millimeter).

Figure 9:
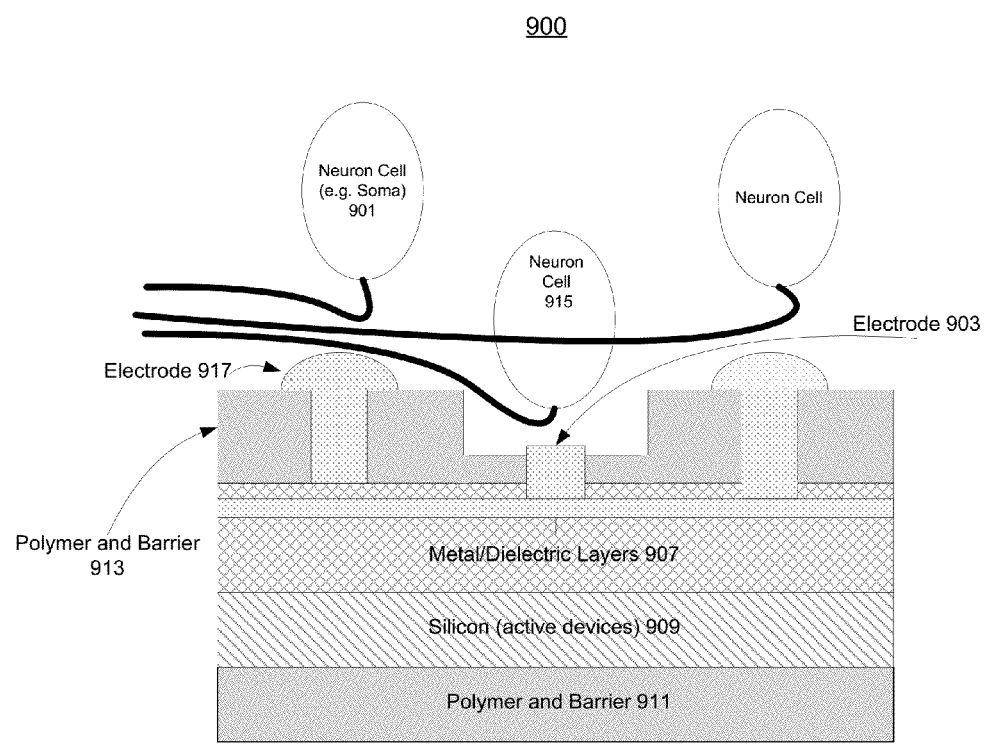
FIG. 9 is a block diagram illustrating layered structures in flexible devices with multi-level electrodes in one embodiment of the present invention.

FIG. 9 is a block diagram illustrating layered structures in flexible devices with multi-level electrode heights in one embodiment of the present invention. For example, device 900 may comprise flexible and integrated chip with arrays of electrode protruding in multi-levels. Device 900 may include layered structures having metal/dielectric layers 907, silicon with active components 909, and polymer and barrier layers 913 wrapping the device with the polymer and barrier layers 911. Electrodes 917, 903 may be positioned in two different levels to separately stimulate neuron cells 901, 915.

In one embodiment, multiple-level protruding electrodes, such as electrodes 917, 903, may differentially stimulate different strata in different types of neuron cells (e.g. ON type cells, OFF type cells, or other applicable types of cells). For example, multiple-level protruding electrodes may separately target neurons ON-pathway and OFF-pathway as retina connections between bipolar cells and ganglion cells separated into two different levels of strata.

Figure 10A:
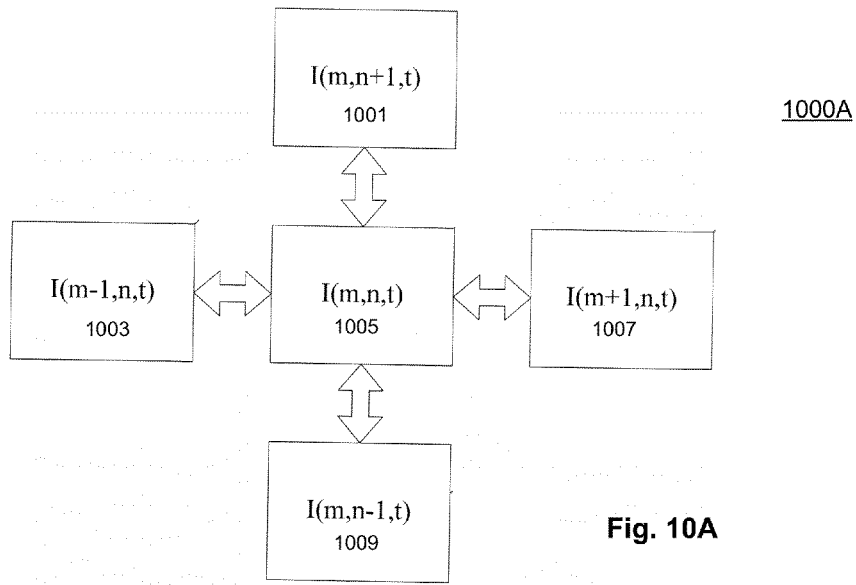
FIGS. 10A-10B are schematic diagrams illustrating exemplary signal processing circuitry in flexible devices according to one embodiment of the present invention.
Figure 10B:
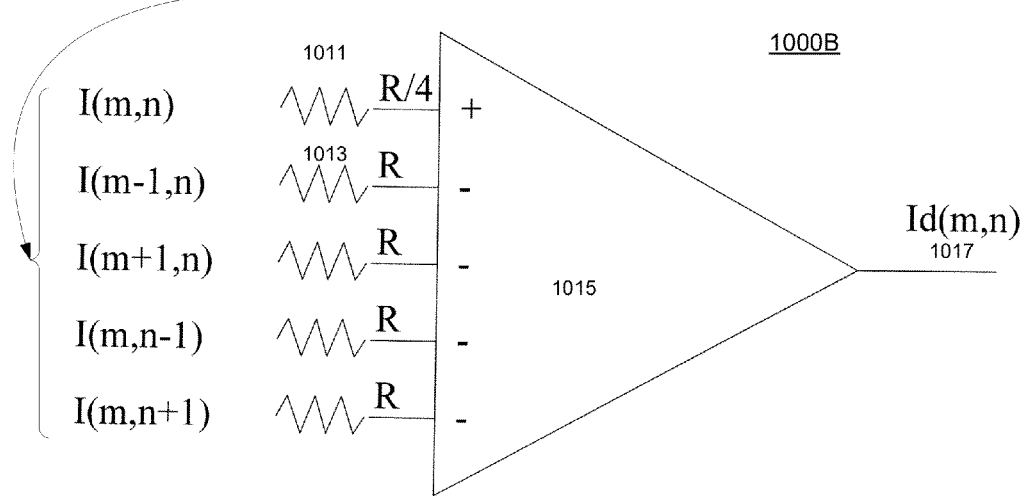

FIGS. 10A-10B are schematic diagrams illustrating exemplary signal processing circuitry in flexible devices according to one embodiment of the present invention. Device 1000A of FIG. 10A may include pixel unit 1005 coupled with neighboring pixel units 1001, 1003, 1007, 1009 in a two dimensional pixel unit array. Pixel unit 1005 may be indexed by (m, n) in the two dimensional pixel unit array to receive incoming light at time t represented by I(m, n, t). Each pixel unit may exchange information on received light with neighboring units (or other applicable pixel units).

In one embodiment, each pixel unit may include signal processing circuitry to receive inputs from neighboring pixel units. For example, referring to FIG. 10A, signals I(m, n+1, t), I(m−1, n, t), I(m, n−1, t), and I(m+1, n, t) representing light received or sensed from neighboring pixel units 1001, 1003, 1007, 1009 may be available to pixel unit 1005. The arrangement of pixel units may be based on rectangular, hexagonal (e.g. with each pixel unit having six closes neighbor pixel units), or other applicable two dimensional or multi-dimensional array.

In certain embodiments, a flexible integrated device may include signal processing circuitry capable of simulating neuron network processing mechanisms similar to the center/surround antagonism receptive field of neurons. For example, a pixel unit may generate a pixel current output (or a stimulus) proportional to the difference of the sum of center pixel light intensity and the averaged sum of surround light intensity on its neighbors to excite proper RGC spiking. In general, a pixel unit may use different weights to sum over inputs from local coupled neighboring pixel units, such as those closest neighbors, second closest neighbors, third closest neighbors, etc. to derive a processed signal derived from captured light for generating a stimulus.

For example, circuitry 1000B of FIG. 10B may include a processing element 1015 generating a weighted output Id(m, n) 1017 from sensed signal inputs 1019 separately weighted through weigh settings 1011, 1013 (e.g. resistor components). In one embodiment, pixel unit 1005 of FIG. 10A may include circuitry 1000B for signal processing. Four of sensed signals I(m−1, n), I(m+1, n), I(m, n−1), I(m, n+1) 1019 (e.g. inputs from neighboring pixel units) may be weighted with equal weights of 1/4 of sensed signal I(m, n) via resistor components, such as R 1013 and R/4 1011. In some embodiments, weights may be set (e.g. dynamically configured) to about zero (e.g. equivalent to disconnecting from corresponding neighboring pixel units) for a majority of neighboring pixel units except for those pixel units at metering locations to reduce effect of background absolute light intensity in a similar manner as multi-point metering used in digital cameras. In some embodiments, signal subtraction may be applied in processing signals exchanged from neighboring pixels units to generate stimuli based on relative intensity of incoming light instead of absolute intensity.

Figure 11A:
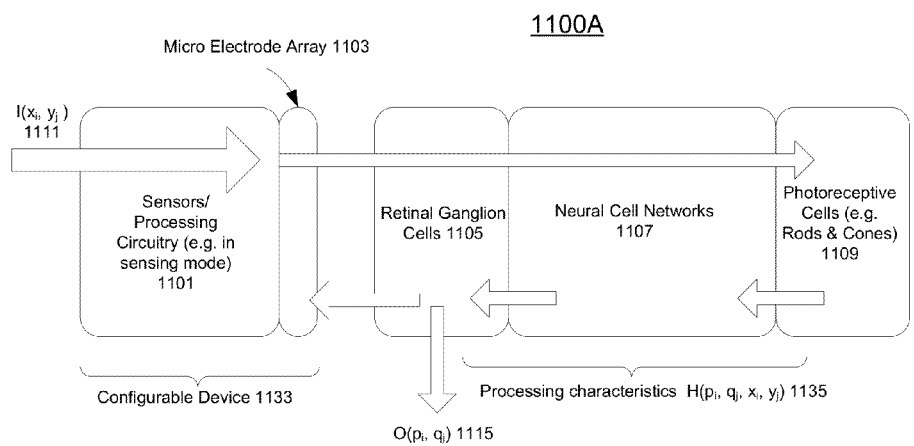
FIGS. 11A-11B are block diagrams illustrating operations of configured flexible devices in one embodiment of the present invention.
Figure 11B:
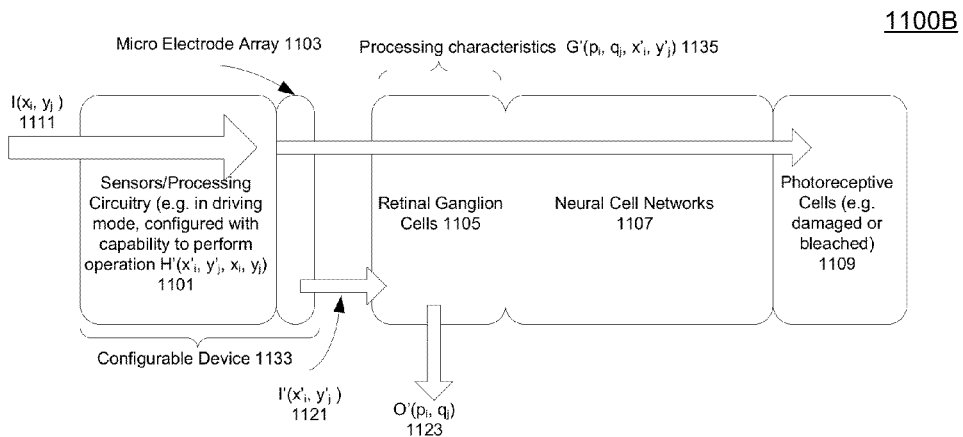

FIGS. 11A-11B are block diagrams illustrating operations of configured flexible devices in one embodiment of the present invention. For example, flexible integrated device 1133 may be configurable to provide portions of functionality identified from neuron cells, such as retinal ganglion cells 1105 and/or neural cell networks 1107, to reestablish damaged or deteriorated vision perception. Neural cell networks 1107 may include neuron cells such as horizontal cells, bipolar cells, amacrine cells or other retina cells etc. Device 1133 may include processing circuitry 1101 coupled with micro electrode array 1103 capable of sending stimuli to and/or sensing responses from neuron cells.

In one embodiment, device 1133 may be configurable when operating in a calibration/programming mode. Device 1133 may operate in other modes such as a normal mode to stimulate neuron cells from incoming light to enable vision perception. In some embodiments, during a calibration/programming mode, sensor and processing circuitry 1101 may switch between a sensing mode and a driving mode to identify and configure processing characteristics (e.g. via a programmable logic array or other applicable programmable circuitry) such that proper stimuli can be generated for desired sensory output O(pi, qi) 1115 from incoming light I(xi, yi) 1111 (e.g. generated light) when a portion of the neuron cells are unable to function properly (e.g. damaged, decayed, deteriorated etc.)

For example, sensor and processing circuitry 1101 may enter a sensory mode right after sending stimulus from incoming light I(xi, yi) 1111 to normal working or relatively healthy neuron cells to produce sensory output O(pi, qi) 1115. In some embodiments, light I(xi, yi) 1111 may be generated to optically select and configure a portion (e.g. a pixel unit or a group of pixel units) of device 1133. Processing circuitry 1101 in the sensing mode may be capable of detecting responses from the neuron cells, such as retinal ganglion cells 1105. The responses may be voltages, waveforms or other applicable signals or spikes over a period of time to represent sensory output O(pi, qi) 1115. Processing circuitry 1101 may store information including relationship between incoming light and the corresponding responses detected. The information may represent inherent processing characteristics H(pi, qj, xi, yi) 1135 in neuron cells, for example, based on the relationship indicated by the expression $O=H*I$.

Subsequently, as shown in FIG. 11B, processing circuitry 1101 may be configured to perform operations to make up for lost or altered visual information processing capabilities of neuron cells. For example, photoreceptive cells 1109 may be damaged or bleached to block neural cell networks 1107 from processing sensed light signals. As a result, visual perception may be based on processing characteristics G' (pi, qj, x'i, y'j) 1135 of retinal ganglion cells 1105.

In one embodiment, processing circuitry 1101 may be configured (e.g. automatically or manually) to perform operation (or transform operation) H'(x'i, y'j, xi, yj). For example, stimuli to retina ganglion cells 1105 may be generated in the configured processing circuitry 1101 according to effective light input $I'=H'*I$ to allow perceived output O'(pi, qj) 1123 according to $G'*I'$ to be close to O(pi,qj) 1115. In one embodiment, H'(x'i, y'j, xi, yj) may be programmed or configured based on inherent processing characteristics H(pi, qj, xi, yj). Processing circuitry 1101 may operate in a driving mode with the configured processing capability. Device 1133 may operate in a normal mode of operation, or in a calibration mode of operation for further fine tuning or adjustment.

In one embodiment, processing circuitry may incorporate electrical sensing circuitry to enable measurement of retina neuron response kinetics during a calibration mode, for example, when device 1133 is implanted in an epi-retina manner. With the ability to switch the device (or chip) to electrical sensing right after electrical stimulation, the ON cells and OFF cells can be identified through the response time, and this information can be used to formulate the specific electrical stimulus from the nearby electrode when local light information is sensed by photo sensors on the device.

Figure 12:
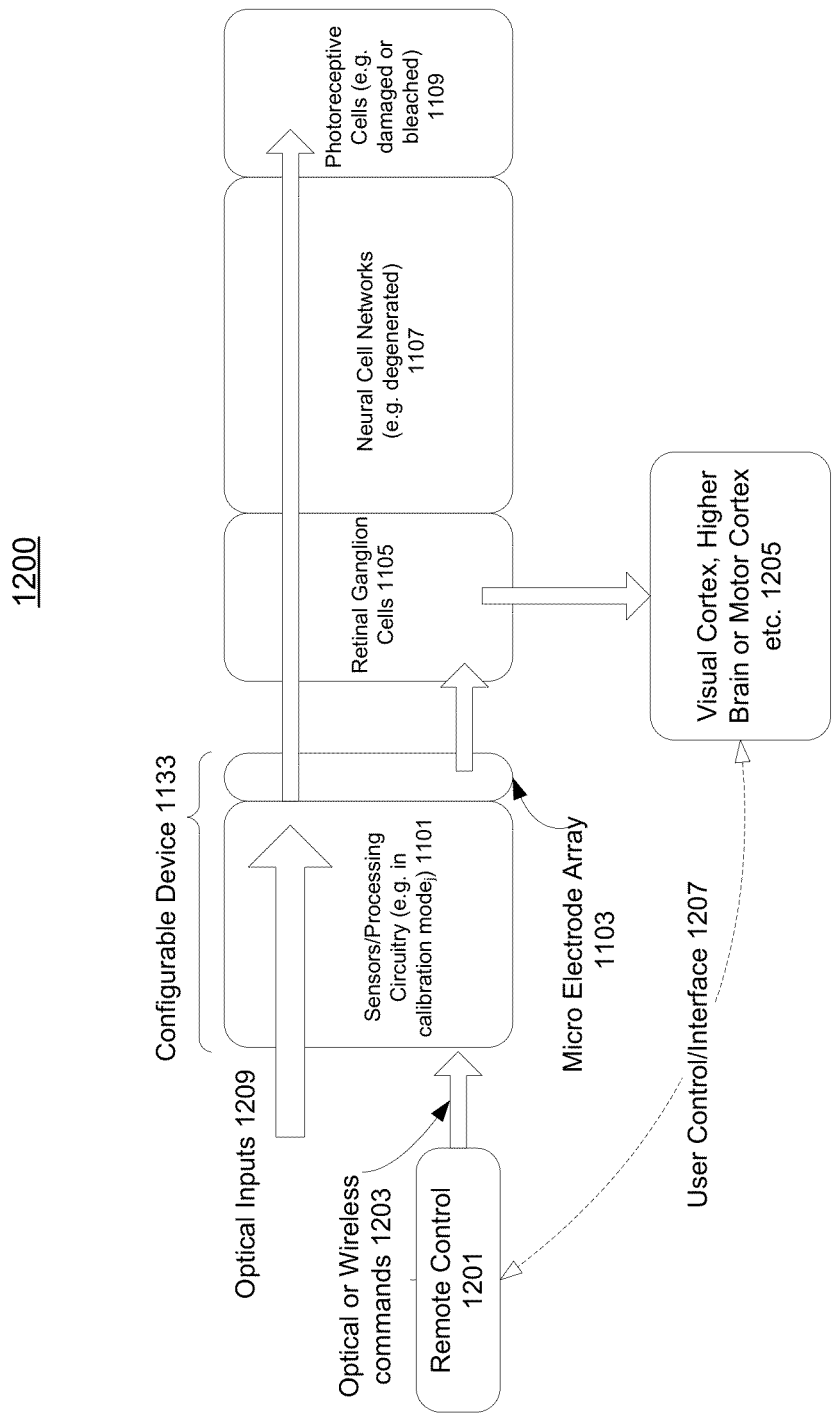
FIG. 12 is a block diagram illustrating a system to calibrate and tune the flexible devices in one embodiment of the present invention.

FIG. 12 is a block diagram illustrating a system to configure flexible devices in one embodiment of the present invention. System 1200 may include configurable retinal prosthesis device 1133 with on-chip processing circuitry 1101 optically or wirelessly coupled with external or remote control device 1201 to provide a control or feedback path for tuning/adjusting configurable device 1133. In one embodiment, processing circuit 1101 and electrode array 1103 may include electrical parameters or settings which can be updated via external commands, for example, to adjust light sensitivity, stimulus intensity, or other applicable parameters to individual pixel level and achieved desired visual perception. In one embodiment, a patient may operate remote control 1201 via user control 1207 based on perceived visions in visual cortex 1205.

In some embodiments, external commands 1203 may be optical commands included in optical inputs 1209 which may comprise predetermined visual patterns. Alternatively, external commands 1203 may be wirelessly transmitted (e.g. based on EM signals or RF signals) to device 1133 via wireless transceiver. Device 1133 may include certain light sensing pixels together with special decoding circuit on chip to detect special light pulse pattern from optical input 1203 to enter the chip into calibration mode for tuning/adjustment. Alternatively, the external commands may wirelessly cause device 1133 to enter a calibration mode or other modes of operation.

In one embodiment, each pixel or regions of pixels of device 1133 may be separately accessed optically or wirelessly through light projection (e.g. into the eye on the implanted region). The pixel or regions can be electrically accessed on chip to tune electrical stimulus parameters to achieve targeted effects of visual sensation. In one embodiment, test patterns, e.g. via optical input 1209, can be projected onto the implanted retina or directly viewed by implanted patients. The targeted visual effects may be described to the patients for conducting manual tuning of parameters of implanted retina prosthesis chips using the external optical input device to allow the best approximation of the targeted visual effects.

FIG. 13 is a flow diagram illustrating a method to configure flexible devices in one embodiment described herein. Exemplary process 1300 may be performed by a processing circuitry that may comprise hardware (circuitry, dedicated logic, etc.), software (such as machine code executed in a machine or processing device), or a combination of both. For example, process 1300 may be performed by some components of system 1200 of FIG. 12.

In one embodiment, the processing logic of process 1300 may detect light patterns (e.g. predetermined) from received light via photo sensors at block 1301. The processing logic of process 1300 may decode the captured light to extract the light patterns optically encoded in the light. On detecting the light patterns, the processing logic of process 1300 may cause a device to enter a calibration mode for configuration. The device may comprise an array of pixel units to receive light to enable perception of a vision from the light. The pixel units may include circuitry configurable via electrical parameters, such as detection circuitry for photo sensors and/or driving circuitry for electrodes.

At block 1303, in one embodiment, the processing logic of process 1300 may receive light patterns to select pixel units from an array of pixel units of a flexible integrated device. The light patterns may be associated with known effects of visual sensation. For example, a patient implanted with the device may be aware of which visual perception to be expected, such as the shape of the image of light, the relative intensity of the image of light or other visual effects. At block 1305, the processing logic of process 1300 may generate stimuli from selected pixel units to stimulate neuron cells to cause actual effect of visual sensation similar to a normal person should experience with the light patterns received. In some embodiments, the light patterns may include selection light patterns to identify which pixel units should be selected.

Subsequently, at block 1307, in one embodiment, the processing logic of process 1300 may receive external commands to update electrical parameters of a flexible integrated device. The external commands may be optically or wirelessly received. The processing logic of process 1300 may update the electrical parameters to cause adjustment of actual effects of visual sensation from the light patterns (or other applicable incoming light) received via the selected pixel units updated with the electrical parameters. The captured light (e.g. the light patterns) may be associated with known visual effects. As a result of the update, the actual effect of visual sensation may be adjusted to match the known effects of visual sensation to proper configure the device. In some embodiments, light patterns may be separately generated for pixel selection and for electrical or circuitry updates for the selected pixels.

In the foregoing specification, the invention has been described with reference to specific exemplary embodiments thereof. It will be evident that various modifications may be made thereto without departing from the broader scope of the invention as set forth in the following claims. The invention is not limited to the particular forms, drawings, scales, and detailed information disclosed. The specification and drawings are, accordingly, to be regarded in an illustrative sense rather than a restrictive sense.

What is claimed is:

1. An implant apparatus comprising:
    a plurality of pixel units arranged over a semiconductor device with a front side and a back side, each pixel unit comprising:
        a photo sensor to receive light,
        a micro electrode, and
        circuitry coupled to the photo sensor and the micro electrode,
    wherein the photo sensors, the micro electrodes and the circuitry of the pixel units are embedded within one or more layers of material based on a silicon substrate of the semiconductor device, the layers including a semiconductor layer formed via the front side within the silicon substrate, the photo sensors and the circuitry embedded within the semiconductor layer, the circuitry to drive the micro electrodes to stimulate neuron cells for enabling perception of a vision of the light captured by the photo sensors,
    wherein thickness of the silicon substrate is sized to allow the photo sensors to capture the light from either the front side or the back side,
    wherein the thickness of the silicon substrate is sized for a flexibility of the semiconductor device to conform to a shape of a human eyeball and allow the micro electrodes in close proximity to the neuron cells for the stimulation, and
    wherein the pixel units are configured to capture the light for driving the neuron cells within the close proximity with number of the photo sensors per square millimeter higher than 250.

2. The apparatus of claim 1, wherein each micro electrode is sized to target a small number of separate neuron cells.

3. The apparatus of claim 1, wherein the neuron cells are distributed in a quasi-spherical geometry based on the shape of a human eyeball, and wherein the semiconductor device is flexible to conform to the quasi-spherical geometry.

4. The apparatus of claim 1, wherein the semiconductor device includes one or more modules, each module including one or more of the pixel units, wherein boundaries between adjacent modules are perforated with perforation holes.

5. The apparatus of claim 1, where the pixel units have a density higher than 1000 per square millimeter.

6. The apparatus of claim 1, wherein the semiconductor device further comprises layered structures including the semiconductor layer and metal interconnect layers, wherein the semiconductor layer includes the photo sensors and transistors for the circuitry, and wherein the micro electrodes are separate from the semiconductor and metal interconnect layers, the micro electrodes coupled with the circuitry via the metal interconnect layers.

7. The apparatus of claim 6, wherein the layered structure includes a substrate layer, wherein the semiconductor layer is positioned in the layered structure close to the front side of the semiconductor device and wherein the substrate layer is positioned in the layered structure close to the back side of the semiconductor device opposite to the front side.

8. The apparatus of claim 4 wherein the boundaries between adjacent modules are configured with metal lines without integrated circuit material to add additional modality for the device.

9. The apparatus of claim 7, wherein the micro electrodes are arranged to allow the neuron cells to be in contact with the micro electrodes from the front side of the semiconductor device.

10. The apparatus of claim 7, wherein the micro electrodes are arranged to allow the neuron cells to be in contact with the micro electrodes from the back side of the semiconductor device, wherein the layered structures include through-silicon vias to join the metal interconnect layer and the micro electrodes.

11. The apparatus of claim 10, wherein the photo sensors are arranged to overlap with the micro electrodes between the frond side and the backside of the semiconductor device, the micro electrodes without blocking the light to reach the photo sensors in the semiconductor layer from the back side.

12. The apparatus of claim 11, wherein the thickness is controlled to be several microns to less than several tens microns to allow the sensors to absorb the light through the substrate.

13. The apparatus of claim 12, wherein the substrate has the thickness of about less than 20 microns.

14. The apparatus of claim 1 wherein the micro electrodes are arranged to protrude from the semiconductor with multi-level heights to stimulate separate types of the neuron cells.

15. The apparatus of claim 4, wherein the stimulation is based on electric flows from the electrodes to the neuron cells, wherein the layered structures include guard rings, and wherein each electrode is surrounded by one of the guard rings to provide local return path to confine an electric flow from the electrode to targeted neuron cells.

16. The apparatus of claim 4, wherein the apparatus is suitable of being implanted within living tissues, and wherein the semiconductor device is sealed within biocompatible layers to provide bi-directional protection between the living tissues and the layered structures.

17. The apparatus of claim 16, wherein at least one of the micro electrodes include protruding tips over the biocompatible layer to increase proximity between the at least one electrodes and targeted neuron cells.

18. The apparatus of claim 17, wherein the protruding tips are arranged in one or more protruding layers of different heights above a surface of the semiconductor device to allow micro electrodes of different layers to access different layers of the neuron cells.

19. The apparatus of claim 1, wherein the circuitry includes a plurality of processing circuitry, each pixel unit including one of the plurality of processing circuitry, wherein the pixel units are arranged as a network with interconnects to allow processing circuitry of each pixel unit to derive a stimulus form the light received via the pixel unit and at least one other pixel unit of the network via the interconnects.

20. The apparatus of claim 19, wherein the pixel unit is associated with at least one neighboring pixel units according to the array and wherein the at least one other pixel units include the neighboring pixel units of the pixel unit.

21. An apparatus implementable to tissues including neuron cells, comprising:
a plurality pixel units arranged in a two dimensional array to enable perception of a vision of light incoming to the pixel units, each pixel unit comprising a photo sensor to receive the light, a micro electrode to deliver a stimulus to targeted ones of the neuron cells for the perception, and
circuitry to derive the stimulus from the light and drive the electrode, wherein the photo sensors, the micro electrodes and the circuitry are embedded within one or more layers of material based on a common silicon substrate in a semiconductor device having a front surface and a back surface opposite to the front surface, the layers including a semiconductor layer formed on the front surface within the silicon substrate, the photo sensors and the circuitry embedded within the semiconductor layer, wherein the two dimensional array is arranged within the device including the common silicon substrate; and
biocompatible layers wrapping the device to bi-directionally protect the device and the tissues, the biocompatible layers having openings to allow electrodes of the pixel units to stimulate the neuron cells,
wherein the common silicon substrate of the device is thinned with a thickness to allow the device to be bendable in a two dimensional manner to conform to a shape of a human eyeball and allow the micro electrodes to be in close proximity to the neuron cells,
wherein the thickness of the common silicon substrate is sized to allow the photo sensors to capture the light from either the front surface or the back surface; and
wherein the pixel units are configured to capture the light for driving the neuron cells within the close proximity with a density of the photo sensors higher than 250 per square millimeter.

22. The apparatus of claim 21, further comprising:
a plurality perforation holes through the device to allow fluidic flow between the front surface and the back surface passing through the perforation holes.

23. An integrated circuit device for retina prosthesis, the device comprising:
an array of pixel units to enable perception of a vision of light, wherein the array of pixel units are formed on a common silicon substrate, each pixel unit comprising
a sensor to sense the light,
an electrode to deliver a stimulus to targeted ones of neuron cells for the perception, and circuitry to derive the stimulus from the light to drive the electrode, wherein the sensor, the electrode and the circuitry are embedded within one or more layers of material based on the common silicon substrate in a semiconductor device having a front side and a back side, wherein thickness of the common silicon substrate is sized to allow the sensor to capture the light from either the front side or the back side, wherein the thickness is sized for the device to be bendable to allow the array of pixel units to conform to a radius of curvature no greater than 12.5 millimeter according to a shape of a human eyeball and allow the electrode to be in close proximity to the targeted ones of the neuron cells, and wherein the array of pixel units are arranged to capture the light for driving the neuron cells within the close proximity with a density of higher than 250 per square millimeter.

* * * * *